US012404495B2

(12) United States Patent
Niklason et al.

(10) Patent No.: US 12,404,495 B2
(45) Date of Patent: Sep. 2, 2025

(54) EPITHELIAL CELL DIFFERENTIATION OF HUMAN MESENCHYMAL STROMAL CELLS

(71) Applicant: YALE UNIVERSITY, New Haven, CT (US)

(72) Inventors: Laura E. Niklason, Greenwich, CT (US); Julio J. Mendez, Bridgeport, CT (US)

(73) Assignee: Yale University, New Haven, CT (US)

( * ) Notice: Subject to any disclaimer, the term of this patent is extended or adjusted under 35 U.S.C. 154(b) by 185 days.

(21) Appl. No.: 17/331,257

(22) Filed: May 26, 2021

(65) Prior Publication Data

US 2021/0363492 A1 Nov. 25, 2021

Related U.S. Application Data

(62) Division of application No. 14/911,571, filed as application No. PCT/US2014/050815 on Aug. 13, 2014, now Pat. No. 11,028,367.

(60) Provisional application No. 61/866,570, filed on Aug. 16, 2013.

(51) Int. Cl.
| | | |
|---|---|---|
| C12N 5/071 | (2010.01) | |
| A61K 35/28 | (2015.01) | |
| A61K 35/36 | (2015.01) | |
| A61K 35/42 | (2015.01) | |

(52) U.S. Cl.
CPC ............ *C12N 5/0688* (2013.01); *A61K 35/36* (2013.01); *A61K 35/42* (2013.01); *A61K 35/28* (2013.01); *C12N 2500/25* (2013.01); *C12N 2500/84* (2013.01); *C12N 2500/90* (2013.01); *C12N 2501/11* (2013.01); *C12N 2501/385* (2013.01); *C12N 2501/39* (2013.01); *C12N 2501/395* (2013.01); *C12N 2501/81* (2013.01); *C12N 2506/1353* (2013.01); *C12N 2506/1384* (2013.01); *C12N 2533/52* (2013.01); *C12N 2533/54* (2013.01); *C12N 2533/90* (2013.01)

(58) Field of Classification Search
None
See application file for complete search history.

(56) References Cited

U.S. PATENT DOCUMENTS

| | | |
|---|---|---|
| 5,843,780 A | 12/1998 | Thomson et al. |
| 5,945,577 A | 8/1999 | Stice et al. |
| 5,994,619 A | 11/1999 | Stice et al. |
| 6,200,806 B1 | 3/2001 | Thomson et al. |
| 6,235,970 B1 | 5/2001 | Stice et al. |
| 2008/0317720 A1 | 12/2008 | Nagaya et al. |
| 2012/0064050 A1 | 3/2012 | Calle et al. |
| 2013/0071931 A1 | 3/2013 | Ishikawa |

FOREIGN PATENT DOCUMENTS

| | | |
|---|---|---|
| CN | 102388127 A | 3/2012 |
| JP | 2012516699 A | 7/2012 |
| WO | 2005113748 A2 | 12/2005 |
| WO | 2006112365 A1 | 10/2006 |
| WO | 2006112390 A1 | 10/2006 |
| WO | 2007124594 A1 | 11/2007 |
| WO | 2010091188 A1 | 8/2010 |
| WO | 2011139628 A1 | 11/2011 |
| WO | 2013018851 A1 | 2/2013 |
| WO | 2013106677 A1 | 7/2013 |
| WO | 2014052458 A1 | 4/2014 |

OTHER PUBLICATIONS

Larson et al. Gene Therapy 15 pp. 434-442. 2008.*
European Search Report for European Patent Application No. 14836340.1 issued Dec. 20, 2016.
PCT International Search Report and Written Opinion for PCT International Application No. PCT/US2014/050815 Issued Dec. 12, 2014.
Al-Nbaheen, et al., "Human stromal (mesenchymal) stem cells from bone marrow, adipose tissue and skin exhibit differences in molecular phenotype and differentiation potential", Stem Cell Rev. 9(1), Feb. 2013, 32-43.
Badylak, et al., "Whole-organ tissue engineering: decellularization and recellularization of three-dimensional matrix scaffolds", Annu Rev Biomed Eng. 13, 2011, 27-53.
Baer, et al., "Adipose-derived mesenchymal stromal/stem cells: tissue localization, characterization, and heterogeneity", Stem Cells Int., 2012, 1-11.
Bonvillain, et al., "A nonhuman primate model of lung regeneration: detergent-mediated decellularization and initial In vitro recellularization with mesenchymal stem cells", Tissue Eng Part A. 18, 2012, 2437-2452.
Cortiella, et al., "Influence of acellular natural lung matrix on murine embryonic stem cell differentiation and tissue formation", Tissue Eng Part A. 16(8), Aug. 2010, 2565-2580 (Abstract Only).
Daly, et al., "Initial binding and recellularization of decellularized mouse lung scaffolds with bone marrow-derived mesenchymal stromal cells", Tissue Eng. Part A 18(1-2), Jan. 2012, 1-16.
Delarosa, et al., "Human adipose-derived stem cells impair natural killer cell function and exhibit low susceptibility to natural killer-mediated lysis", Stem Cells Dev. 21(8), May 20, 2012, 1333-1343.
Furuya, et al., "Efficacy of ASC transplantation in elastase-induced pulmonary emphysema model rat", General Subjects (Poster Sessions), Saisei-Iryou (Regenerative Medicine), vol. 10, Suppl, 1P-110, 2011, 219.

(Continued)

*Primary Examiner* — Blaine Lankford
(74) *Attorney, Agent, or Firm* — Saul Ewing LLP; Kathryn Doyle; Alireza Behrooz

(57) ABSTRACT

The present invention relates to the discovery that different stem cell types (e.g., bone marrow-derived mesenchymal stem cells (RM-MSC) and adipose-derived mesenchymal stem cells (AT-MSC)) undergo large changes in lung epithelial marker 5 expression depending on the substrate on which they are cultured. The present invention includes methods and compositions for differentiating of mesenchymal stem cells, such as bone marrow and adipose tissue mesenchymal stem cells, into lung cells, populations of lung cells, and methods of alleviating or treating a lung defect in a subject in need thereof.

7 Claims, 20 Drawing Sheets

Specification includes a Sequence Listing.

(56) References Cited

OTHER PUBLICATIONS

Hoffman, et al., "Lung-derived mesenchymal stromal cell post-transplantation survival, persistence, paracrine expression, and repair of elastase-injured lung", Stem Cells Dev. 20(10), Oct. 2011, 1779-1792 (Abstract Only).
Jarvinen, et al., "Lung resident mesenchymal stem cells isolated from human lung allografts inhibit T cell proliferation via a soluble mediator", J Immunol. 181(6), Sep. 15, 2008, 4389-4396.
Kassmer, et al., "Detection of bone marrow-derived lung epithelial cells", Exp Hematol. 38(7), Jul. 2010, 564-573.
Kotton, et al., "Bone marrow-derived cells as progenitors of lung alveolar epithelium", Development. 128(24), Dec. 2001, 5181-5188.
Kotton, et al., "Derivation of lung epithelium from bone marrow cells", Cytotherapy. 5(2), 2003, 169-73.
Krause, "Bone marrow-derived cells and stem cells in lung repair", Proc Am Thorac Soc. 5(3), Apr. 15, 2008, 323-327.
Krause, et al., "Multi-organ, multi-lineage engraftment by a single bone marrow-derived stem cell", Cell. 105(3), May 4, 2001, 369-377.
Lama, et al., "Evidence for tissue-resident mesenchymal stem cells in human adult lung from studies of transplanted allografts", J Clin Invest. 117(4), Apr. 2007, 989-996.
Lee, et al., "Concise review: Mesenchymal stem cells for acute lung injury: role of paracrine soluble factors", Stem Cells. 29(6), Jun. 2011, 913-919.
Lenssen, et al., "Pulmonary stem cells and the induction of tissue regeneration in the treatment of emphysema", Int J Chron Obstruct Pulmon Dis. 2(2), 2007, 131-139.
Ma, et al., "Bone marrow mesenchymal stem cells can differentiate into type II alveolar epithelial cells in vitro", Cell Biol Int. 35(12), 2011, 1261-1266.
Mendez, et al., "Epithelial cell differentiation of human mesenchymal stromal cells in decellularized lung scaffolds", Tissue Eng Part A. 20(11-12), Jun. 2014, 1735-1746.
Ortiz, et al., "Mesenchymal stem cell engraftment in lung is enhanced in response to bleomycin exposure and ameliorates its fibrotic effects", Proc Natl Acad Sci U S A. 100(14), Jul. 8, 2003, 8407-8411.
Petersen, et al., "Matrix composition and mechanics of decellularized lung scaffolds", Cells Tissues Organs. 195 (3), 2012, 222-231.
Petersen, et al., "Tissue-engineered lungs for in vivo implantation", Science. 329(5991), Jul. 30, 2010, 538-541.

Pevsner-Fischer, et al., "The origins of mesenchymal stromal cell heterogeneity", Stem Cell Rev. 7(3), Sep. 2011, 560-568 (Abstract Only).
Rackley, et al., "Building and maintaining the epithelium of the lung", J Clin Invest. 122(8), Aug. 2012, 2724-2730.
Rasmusson, et al., "Mesenchymal stem cells inhibit the formation of cytotoxic T lymphocytes, but not activated cytotoxic T lymphocytes or natural killer cells", Transplantation. 76(8), Oct. 27, 2003, 1208-1213 (Abstract Only).
Rojas, et al., "Bone marrow-derived mesenchymal stem cells in repair of the injured lung", Am J Respir Cell Mol Biol. 33(2), Aug. 2005, 145-152.
Schmiedl, et al., "Distribution of surfactant proteins in type II pneumocytes of newborn, 14-day old, and adult rats: an immunoelectron microscopic and stereological study", Histochem Cell Biol. 124(6), Dec. 2005, 465-476 (Abstract Only).
Segawa, et al., "Mesenchymal stem cells derived from synovium, meniscus, anterior cruciate ligament, and articular chondrocytes share similar gene expression profiles", J Orthop Res. 27(4), Apr. 2009, 435-441.
Vidal, et al., "Comparison of chondrogenic potential in equine mesenchymal stromal cells derived from adipose issue and bone marrow", Vet Surg. 37(8), Dec. 2008, 713-724.
Wagner, et al., "Can stem cells be used to generate new lungs? Ex vivo lung bioengineering with decellularized whole lung scaffolds", Respirology 18(6), Aug. 2013, 895-911.
Wang, et al., "Characterization of mesenchymal stem cells isolated from mouse fetal bone marrow", Stem Cells. 24 (3), Mar. 2006, 482-493.
Weiss, et al., "Stem Cells and Cell Therapies in Lung Biology and Lung Diseases", Proc Am Thorac Soc. 8(3), Jun. 2011, 223-272.
Wong, et al., "Airway regeneration: the role of the Clara cell secretory protein and the cells that express it", Cytotherapy. 11(6), 2009, 676-687 (Abstract Only).
Wong, et al., "Identification of a bone marrow-derived epithelial-like population capable of repopulating injured mouse airway epithelium", J Clin Invest. 119(2), Feb. 2009, 336-348.
Wong, et al., "Targeted cell replacement with bone marrow cells for airway epithelial regeneration", Am J Physiol Lung Cell Mol Physiol. 293(3), Sep. 2007, L740-752.
Schweitzer, K. S. et al., "Adipose Stem Cell Treatment in Mice Attenuates Lung And Systemic Injury Induced by Cigarette Smoking", Am J Respir Crit Care Med, published Aug. 13, 2010, vol. 183, pp. 215-225, 2011.

* cited by examiner

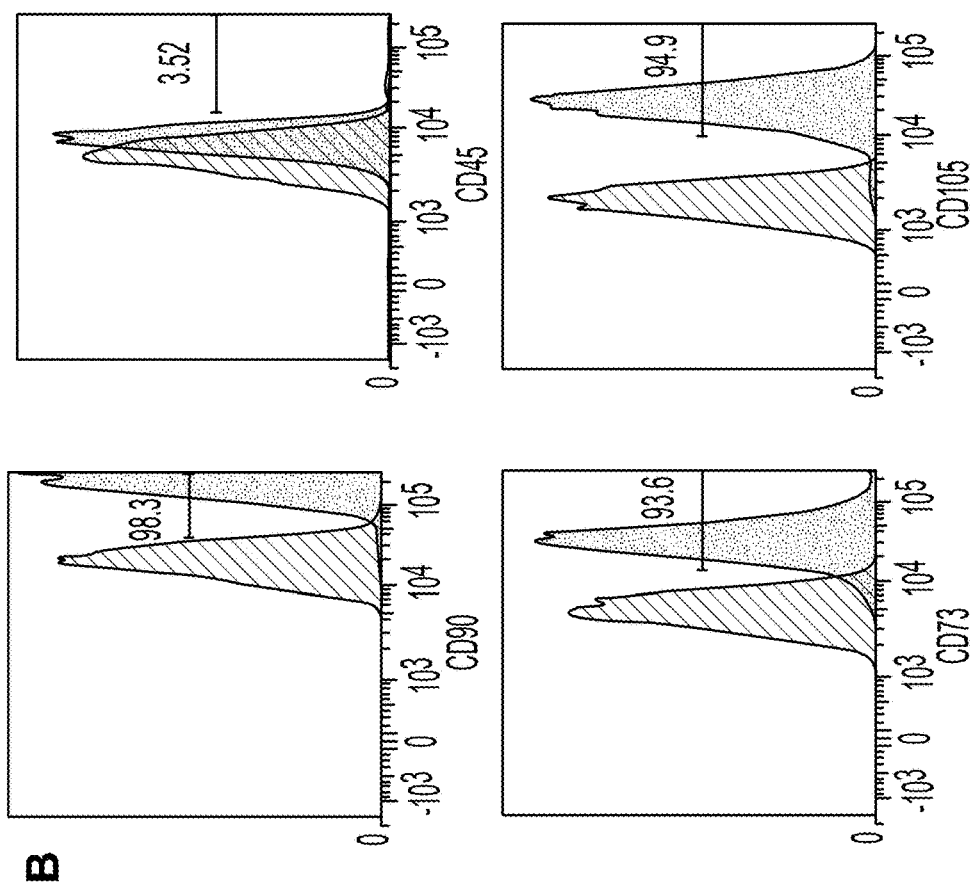
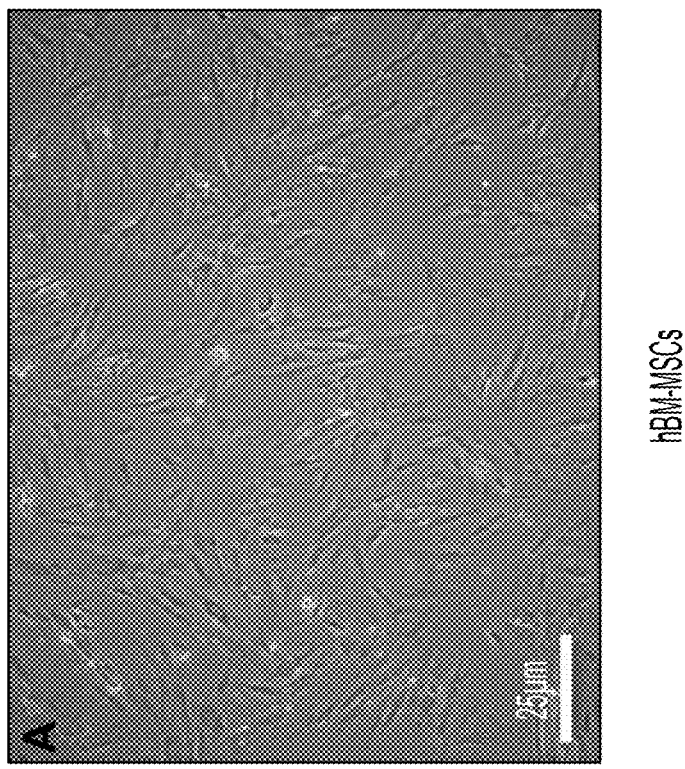
Figure 1A-B

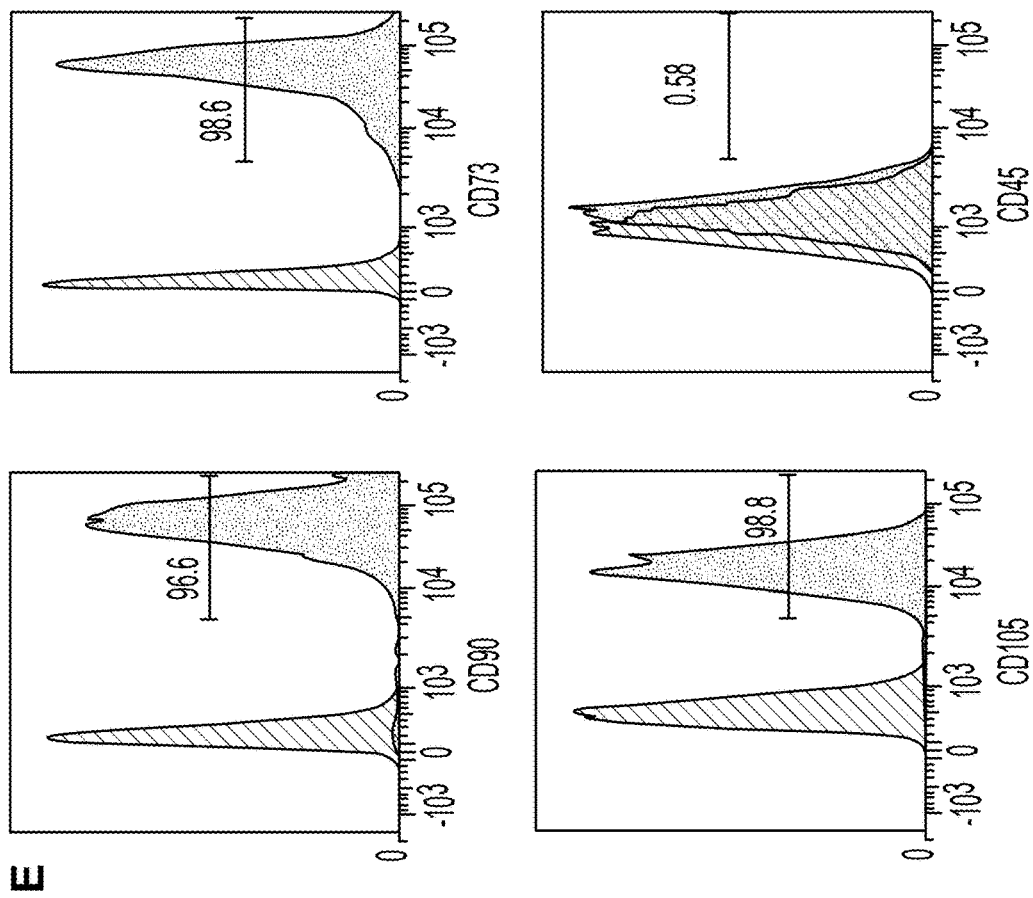
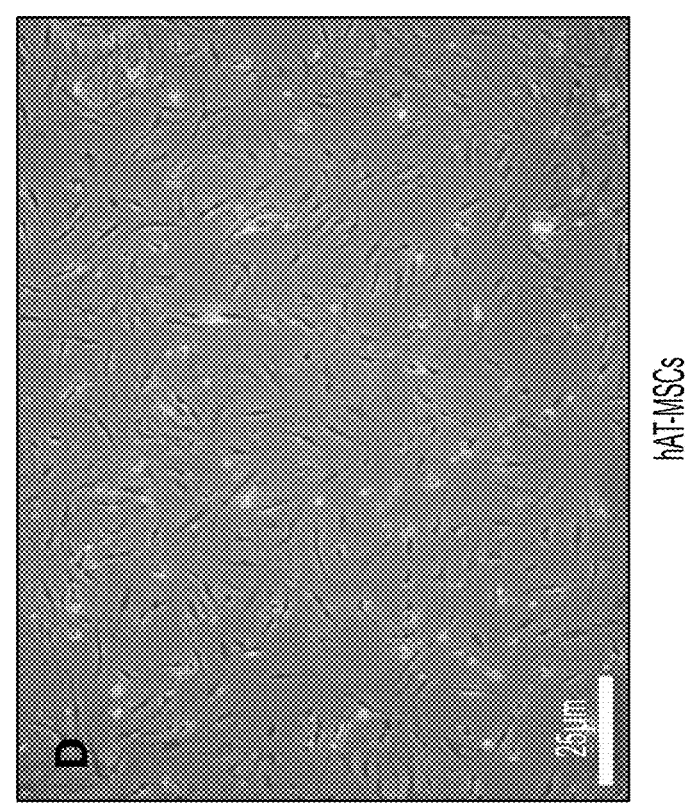
Figure 1D-E

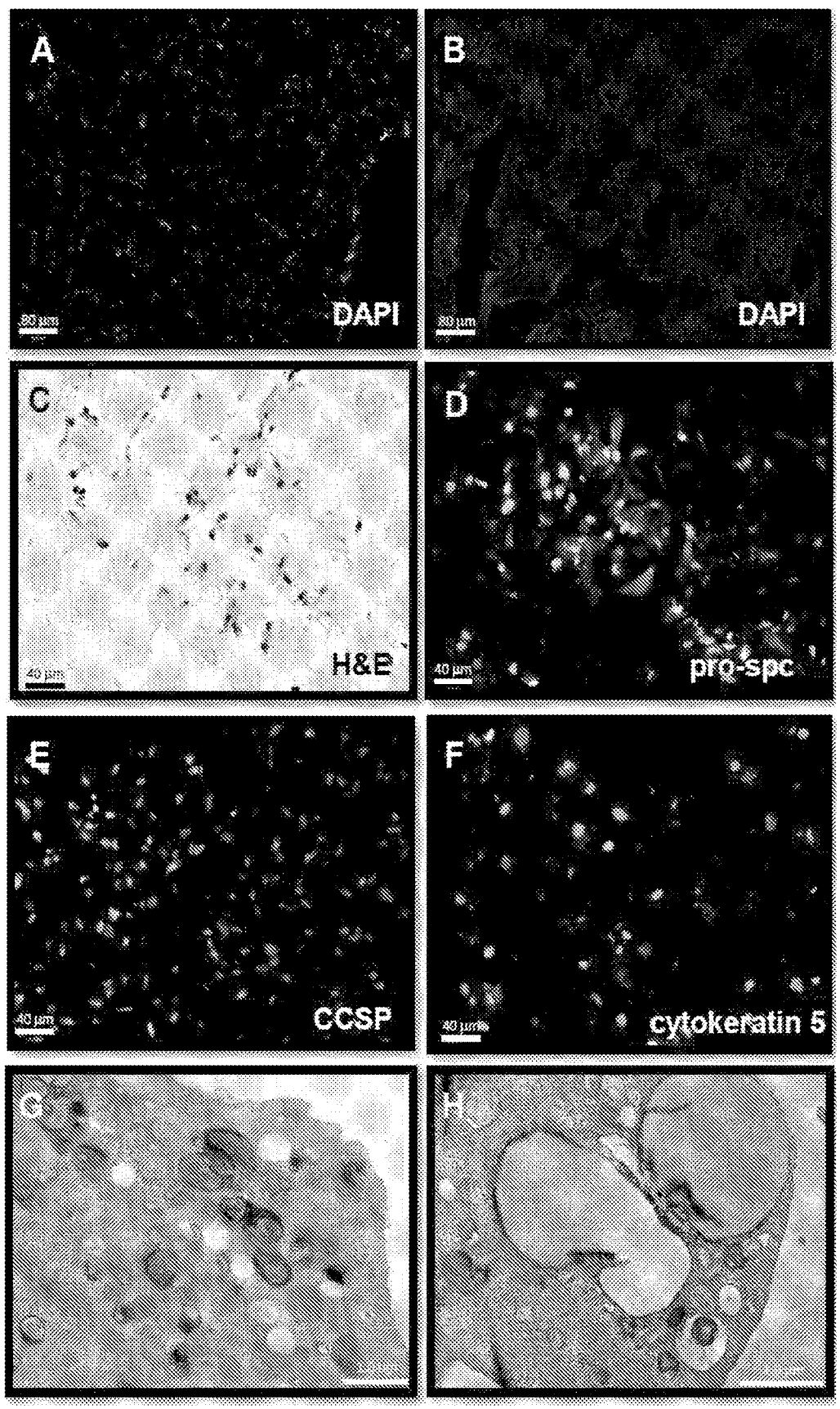
Figure 2A-H

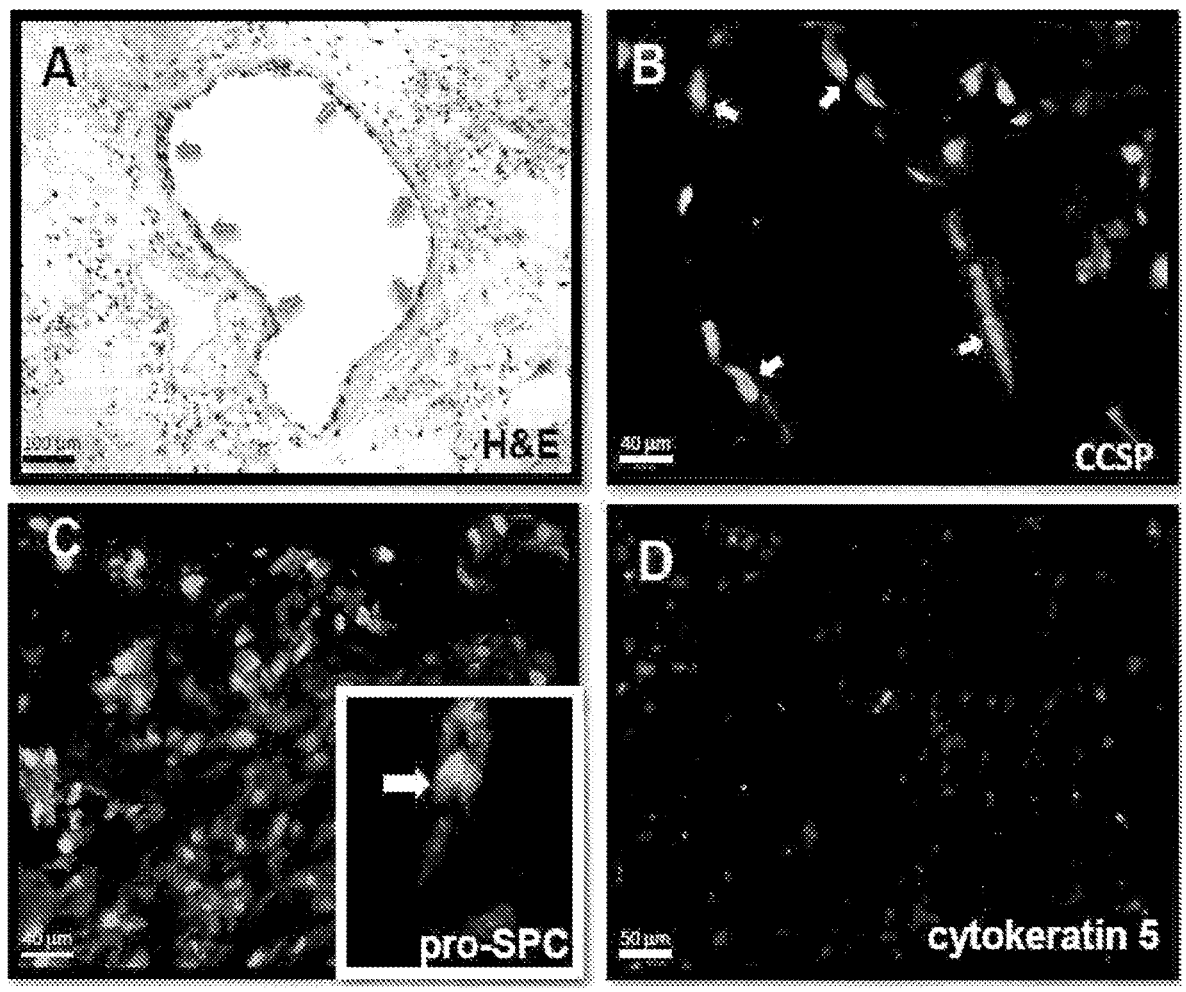
Figure 3A-D

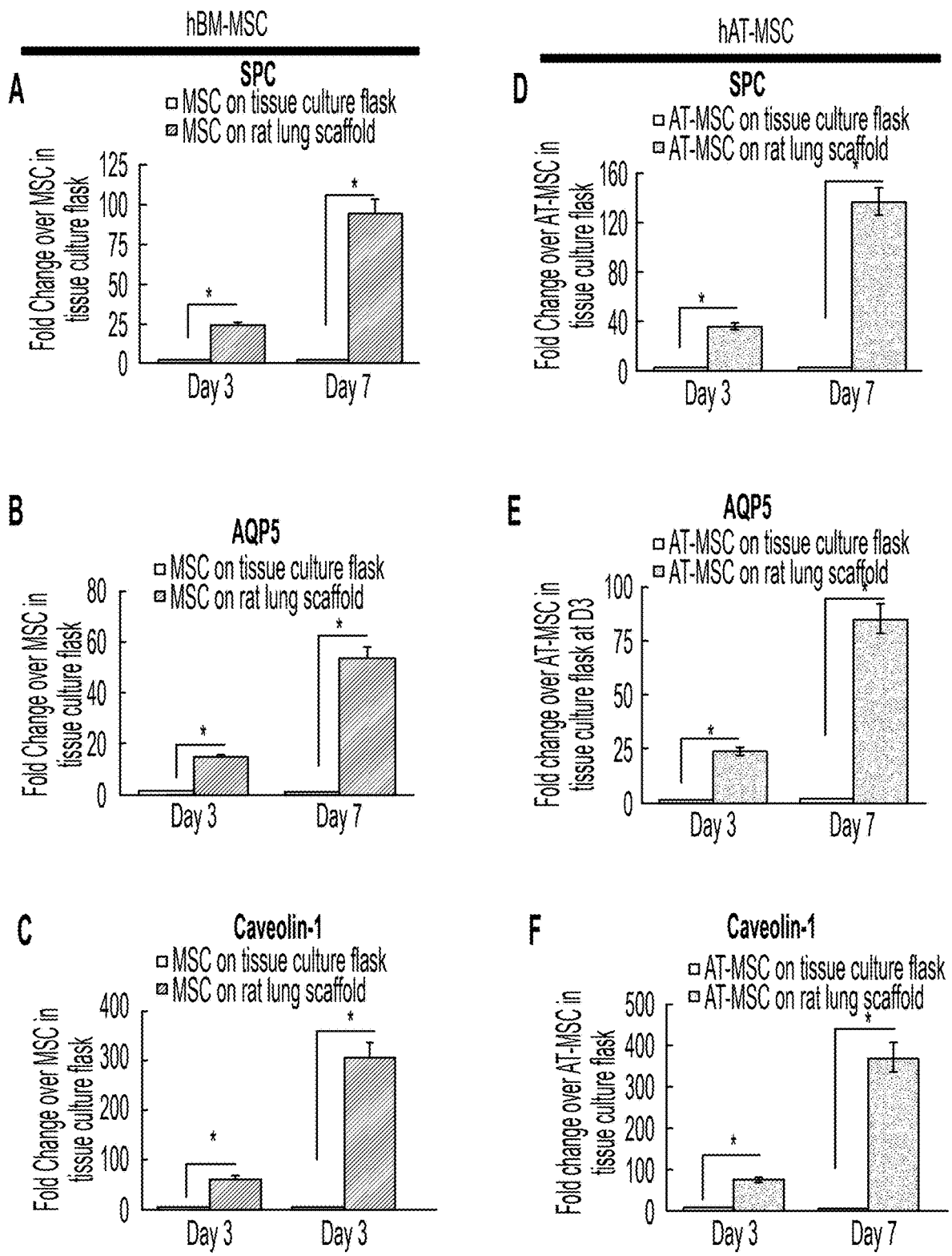
Figure 4A-F

| Gene | Length (bp) | Primer Sequences |
|---|---|---|
| hSPC | 94 | Forward: CCTTCTTATCGTGGTGGTGGT SEQ ID NO: 1<br>Reverse: TCTCCGTGTGTTTCTGGCTCAT SEQ ID NO: 2 |
| Type 1 Markers | | |
| hAQ5 | 79 | Forward: ACTGGGTTTTCTGGGTAGGG SEQ ID NO: 3<br>Reverse: ATGGTCTTCTTCCGCTCTTC SEQ ID NO: 4 |
| hCaveolin-1 | 122 | Forward: CTACAAGCCCAACAACAAGG SEQ ID NO: 5<br>Reverse: CATCGTTGAGGTGTTTAGGGT SEQ ID NO: 6 |
| hGAPDH | 122 | Forward: GACAACAGCCTCAAGATCATCAG SEQ ID NO: 7<br>Reverse: ATGGCATGGACTGTGGTCATGAG SEQ ID NO: 8 |

G (label for table)

Figure 4G

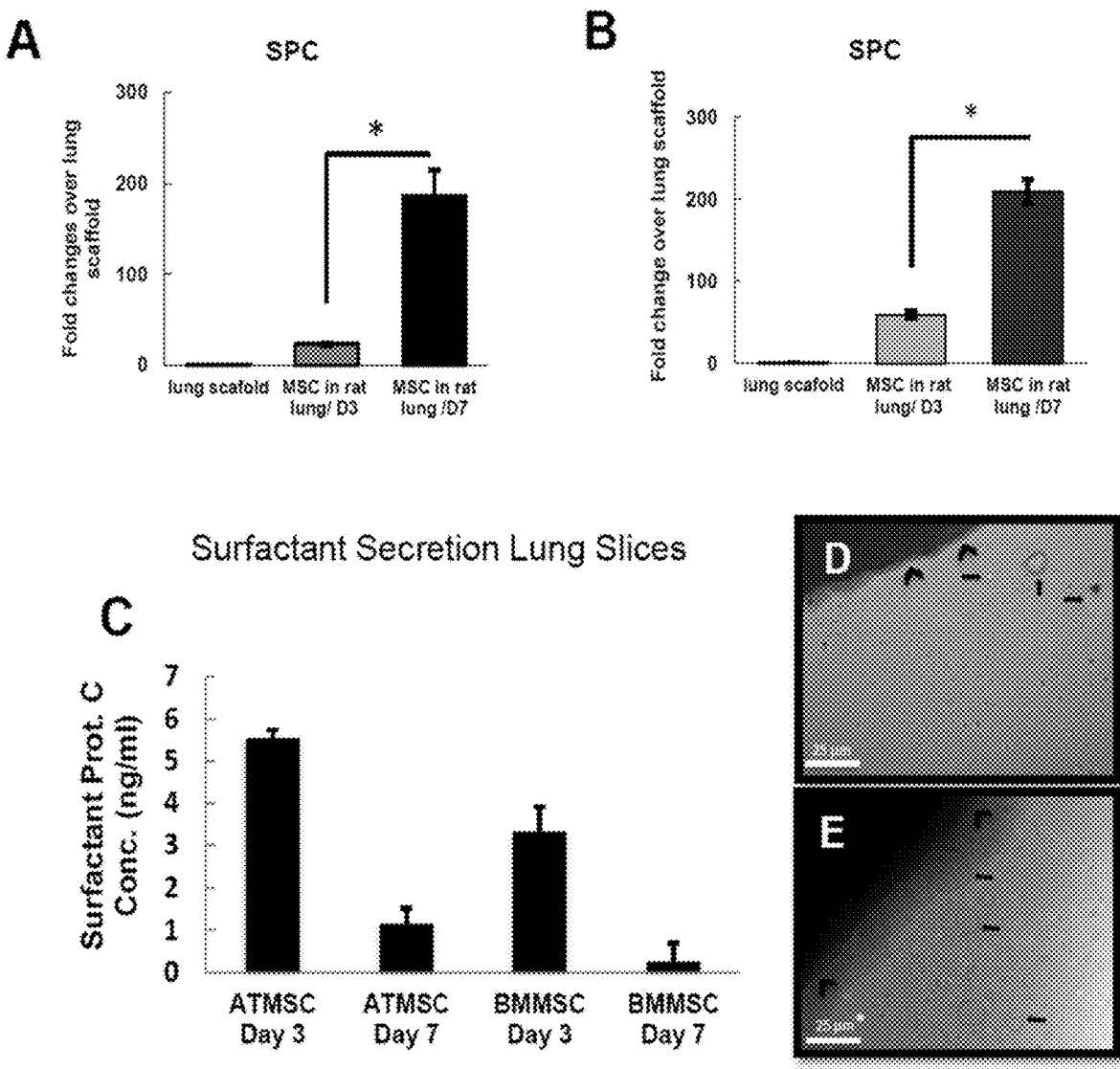
Figure 5A-E

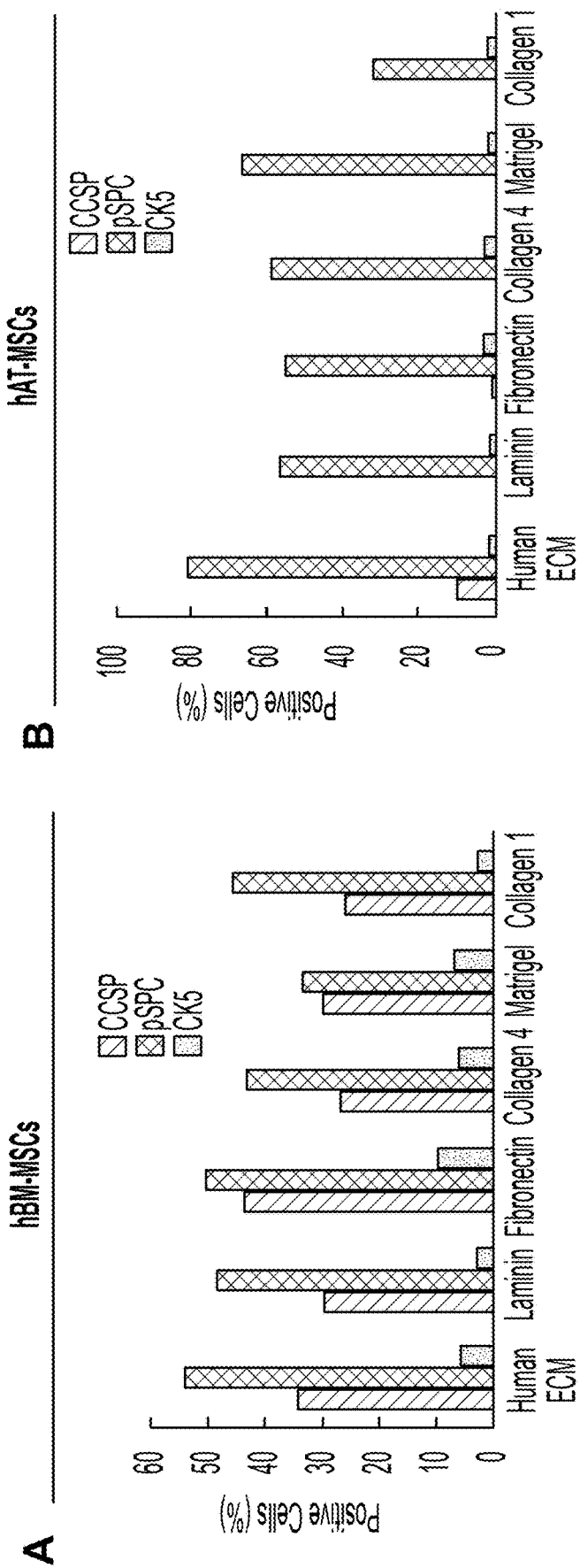
Figure 6A-B

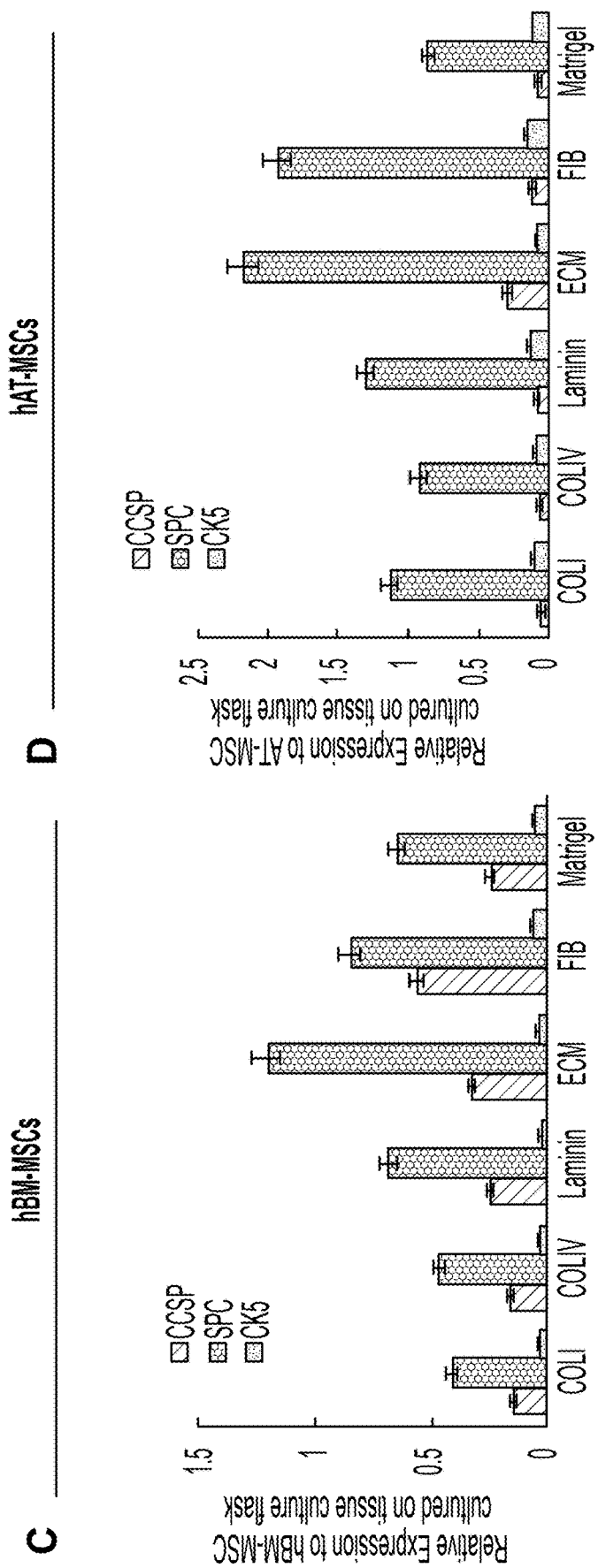
Figure 6C-D

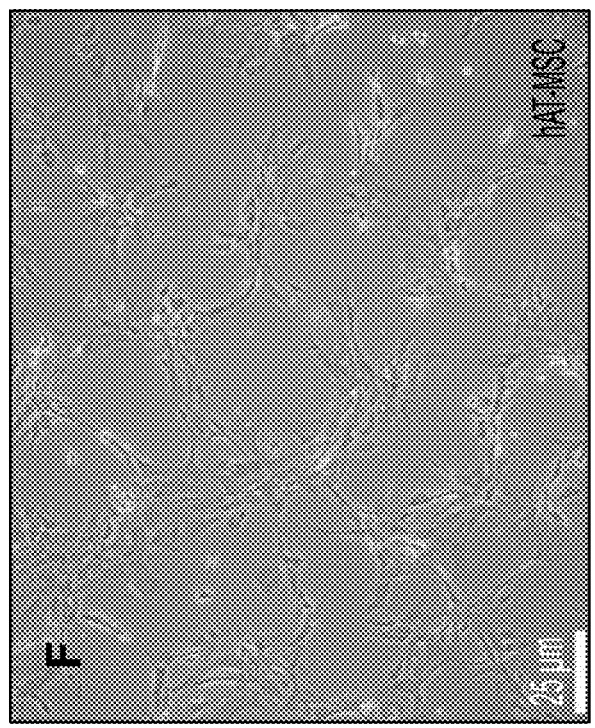
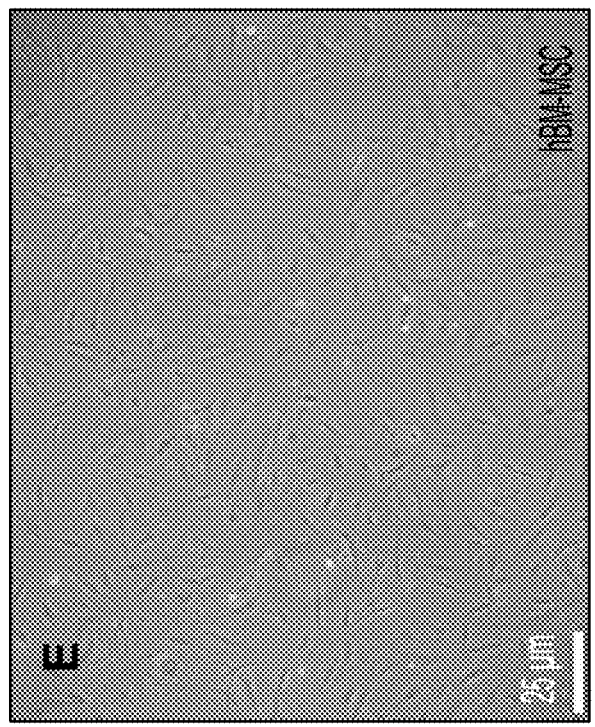
Figure 6E-F

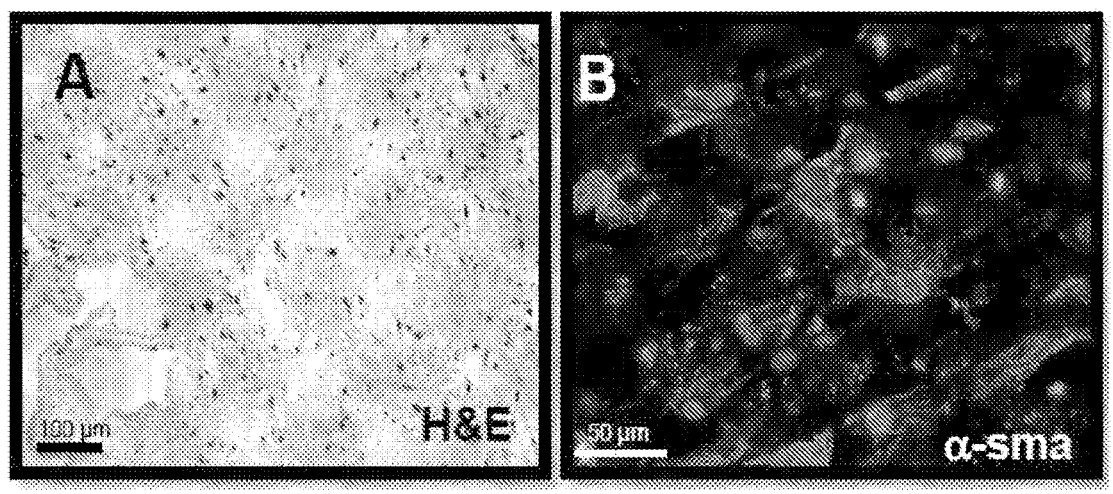
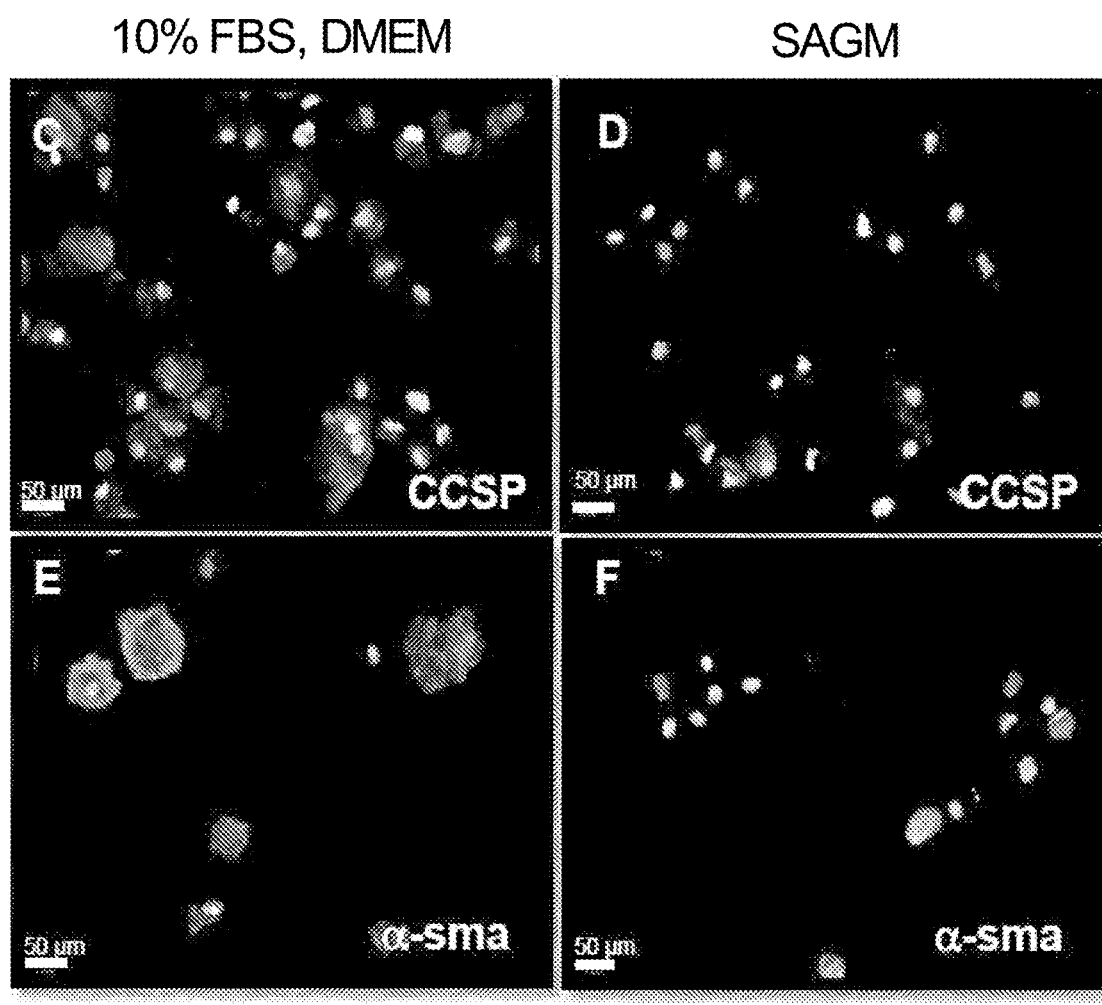
Figure 7A-F

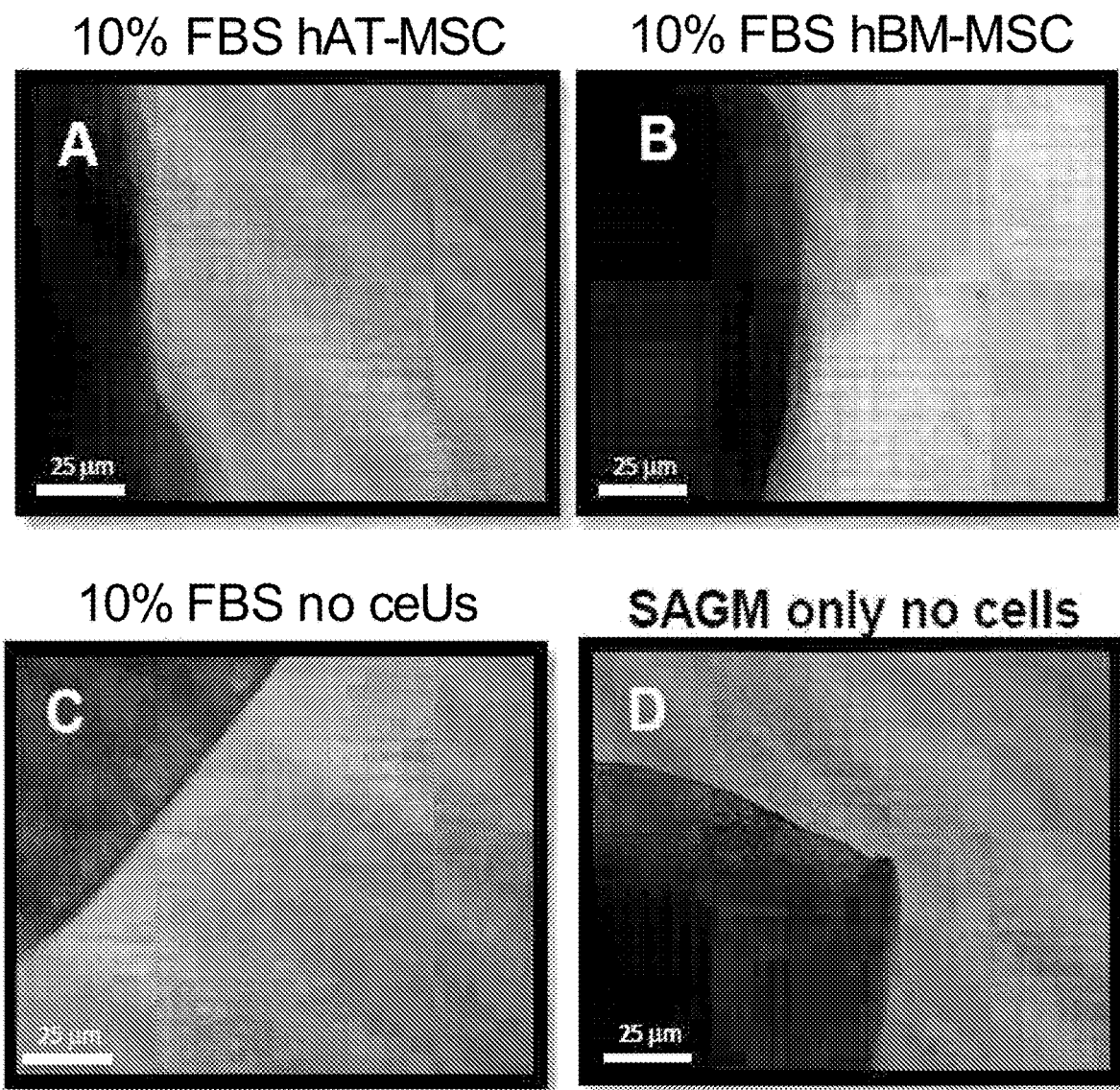
Figure 8A-D

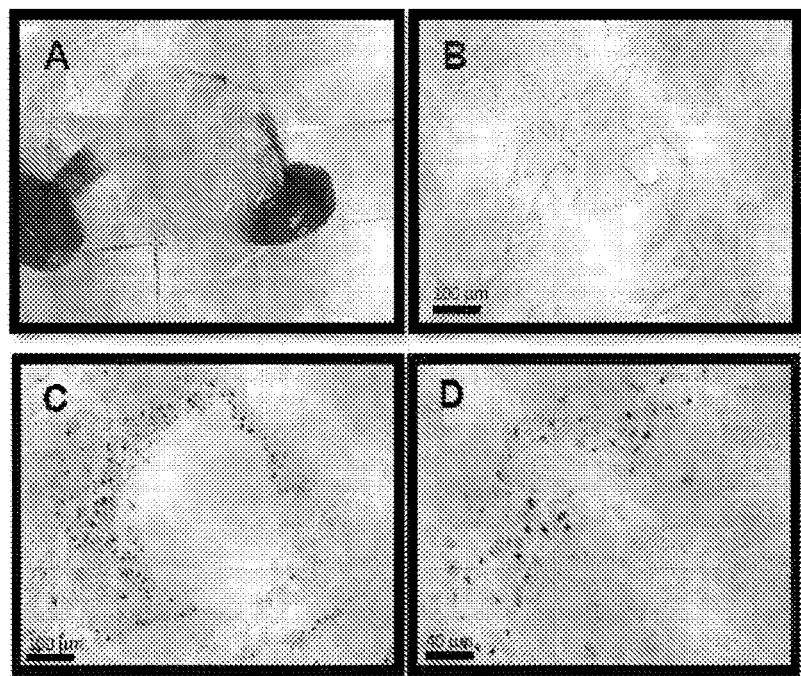
hBM-MSC liver Recell D3 10% FBS/DMEM
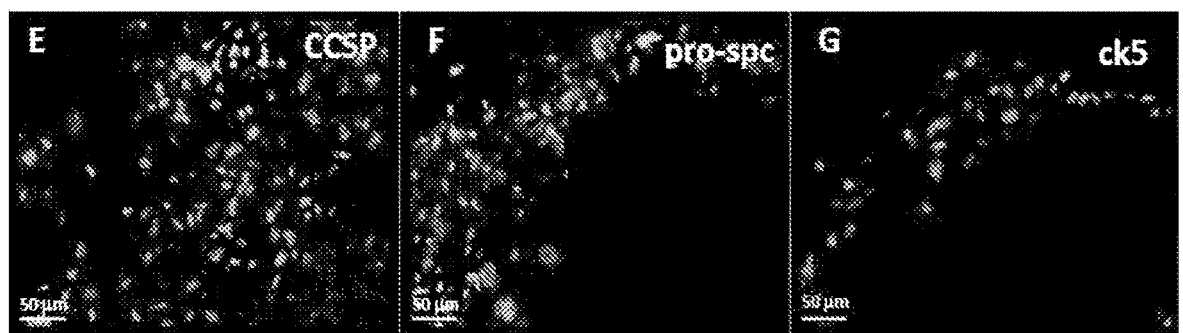
hBM-MSC Liver Recell D3 SAGM
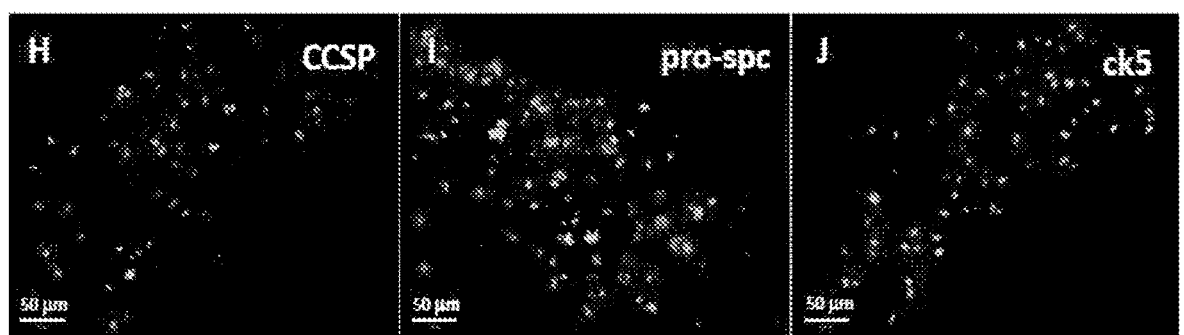
Figure 11A-J

EPITHELIAL CELL DIFFERENTIATION OF HUMAN MESENCHYMAL STROMAL CELLS

CROSS-REFERENCE TO RELATED APPLICATION

This present application is a divisional of U.S. patent application Ser. No. 14/911,571, filed Feb. 11, 2016, now U.S. Pat. No. 11,028,367, which is a U.S. National Phase Application filed under 35 U.S.C. § 371, claiming benefit to International Patent Application No. PCT/US2014/050815, filed on Aug. 13, 2014, which is entitled to priority under 35 U.S.C. § 119(e) to U.S. Provisional Patent Application No. 61/866,570, filed Aug. 16, 2013, each of which application is hereby incorporated herein by reference in its entirety.

STATEMENT REGARDING FEDERALLY SPONSORED RESEARCH OR DEVELOPMENT

This invention was made with government support under GM086287, HL111016 and HL098220 awarded by National Institute of Health. The government has certain rights in the invention.

STATEMENT REGARDING SEQUENCE LISTING SUBMITTED ELECTRONICALLY VIA EFS-WEB

The content of the electronically submitted sequence listing in ASCII text file (Name: 047162-5155US2_Seq_Listing_ST25; Size: 1,800 bytes; and Date of Creation: Aug. 16, 2021) is herein incorporated by reference in its entirety.

BACKGROUND OF THE INVENTION

Various groups have described the capacity for bone marrow derived cells to contribute to lung repair and regeneration (Krause et al., 2001, Cell 105:1-9; Rojas, et al., 2005, Am J Respir Cell Mol Biol 33(2):145-52; Kotton, et al., 2001, Development 128(24):5181-8; Wong et al., 2009, Cytotherapy 11:676-687). Interestingly, these reports show contribution to lung epithelium by the hematopoietic stem cell component of the bone marrow (HSCs) as well as the mesenchymal stromal cell (MSC) fraction. In many of these studies, the contribution by bone marrow derived cells to lung epithelium appears to require lung injury (Krause, 2008, Proc Am Thorac Soc 5:323-327). Of particular interest is that a subpopulation of human and rodent bone marrow MSC-like cells may express Clara cell secretory protein (CCSP), a marker that is associated in the lung with Clara cells (Wong et al., 2009, Cytotherapy 11:676-687). These investigators also showed that tail vein administration of murine CCSP+ bone marrow cells into CCSP knockout mice resulted in the incorporation of CCSP+ cells in the host lung following lung injury.

Bone marrow and adipose tissue derived mesenchymal stromal cells have also been shown to have immunomodulatory roles (DelaRosa, et al., 2012, Stem Cells and Development 21:1333-1343; Rasmusson et al., 2003, Transplantation 76:1208-1213). These include the lack of activation of T cells, as well as a reduction of activated lymphocytes, when MSCs are delivered in animal models in vivo (Rasmusson et al., 2003, Transplantation 76:1208-1213). Additionally, MSCs produce paracrine signals that have also been demonstrated to have anti-inflammatory roles in lung (Lee et al., 2011, Stem Cells 29:913-919; Ortiz et al., 2003, PNAS 100:8408-8411). From a therapeutic standpoint, the evidence favoring the use of MSCs in the potential treatment of lung disease, either via a direct contribution to lung epithelium or through an indirect paracrine immunomodulatory mechanism, is of high interest.

Previous work has utilized neo-natal rodent cells for the repopulation of bioengineered rat lungs (Petersen et al., 2010, Science 329:538-541). These experiments demonstrated the feasibility of using decellularized lungs as a means to direct donor cells to anatomically correct places as well as the resultant functionality, albeit transient, of the repopulated organ. A recent report also described using murine bone marrow derived MSCs that were placed into decellularized mouse lungs (Daly et al, 2012, Tissue Eng Part A 18:1-16). This study failed to show a meaningful contribution by the seeded murine MSCs to adopt a lung epithelial fate. Another study using primate derived MSCs and lung scaffold also did not find conversion of MSCs to a lung epithelial fate after placement on the primate decellularized lung (Bonvillain et al., 2012, Tissue Eng Part A 18(23-24):2437-52).

Thus, there is a need in the art for compositions and methods for epithelial cell differentiation of mesenchymal stromal cells. The present invention addresses this unmet need in the art.

SUMMARY OF THE INVENTION

As described below, the present invention includes methods and compositions for differentiating of mesenchymal stem cells, such as bone marrow and adipose tissue mesenchymal stem cells, into lung cells, populations of lung cells, and methods of alleviating or treating a lung defect in a subject in need thereof.

One aspect of the invention includes a method of differentiating a mesenchymal stem cell (MSC) into a lung cell, the method comprising seeding the MSC on a substrate; and exposing the MSC seeded substrate to growth medium that comprises at least one of retinoic acid and human epidermal growth factor, thereby differentiating the MSC into a lung cell that expresses at least one epithelial.

Another aspect includes a method of modulating the differentiation of a mesenchymal stem cell (MSC) into a lung cell, the method comprising culturing the MSC on a substrate thereby differentiating the MSC into a lung cell.

Yet another aspect includes a population of epithelial lung cells differentiated from mesenchymal stem cells (MSCs), wherein the epithelial lung cells express at least one epithelial marker selected from the group consisting of CCSP, pro-SPC and cytokeratin-5.

Still yet another aspect includes a population of lung cells produced by a method of differentiating a mesenchymal stem cell (MSC) into a lung cell, the method comprising culturing the MSC on a substrate thereby differentiating the MSCs into a lung cell.

In various embodiments of the above aspects or any other aspect of the invention delineated herein, the MSC is selected from the group consisting of bone marrow-derived MSC (BM-MSC) and adipose tissue-derived MSC (AT-MSC). In one embodiment, the lung cell exhibits at least one characteristic of a type II alveolar epithelial cell. In another embodiment, the at least one characteristic of a type II alveolar epithelial cell is expression of at least one epithelial marker selected from the group consisting of pro-SPC and cytokeratin-5. In yet another embodiment, the lung cell exhibits at least one characteristic of a Clara cell. In still another embodiment, the at least one characteristic of a Clara cell is expression of Clara cell secretory protein (CCSP).

In one embodiment, the epithelial lung cells are seeded on a substrate. In another embodiment, the substrate is a decellularized lung tissue. In yet another embodiment, the substrate is a coating comprising an extracellular matrix. In still another embodiment, the extracellular matrix comprises one or more of human ECM, laminin, fibronectin, collagen IV, and collagen I.

In one embodiment, the MSCs are selected from the group consisting of bone marrow-derived MSCs (BM-MSCs) and adipose tissue-derived MSCs (AT-MSCs). In another embodiment, the epithelial lung cells are selected from the group consisting of type I alveolar epithelial cells, type II alveolar epithelial cells and Clara cells.

In another embodiment, the MSC is a bone marrow-derived MSC (BM-MSC), the MSC differentiates into a cell exhibiting at least one characteristic of a type II alveolar epithelial cell. In yet another embodiment, the at least one characteristic of a type II alveolar epithelial cell is expression of at least one selected from the group consisting of pro-SPC and cytokeratin-5.

In another embodiment, the MSC is an adipose tissue-derived MSC (AT-MSC), the MSC differentiates into a cell exhibiting at least one characteristic of a Clara cell. In yet another embodiment, the at least one characteristic of a Clara cell is expression of Clara cell secretory protein (CCSP).

In one embodiment, the population of lung cells comprises genetically modified cells. In another embodiment, the cells are genetically modified to express a therapeutic gene. In yet another embodiment, the genetically modified cells are the epithelial lung cells genetically modified to express a therapeutic gene.

Another aspect includes a method of alleviating or treating a lung defect in a mammal, the method comprising administering to the mammal a therapeutically effective amount of a population of epithelial lung cells differentiated from mesenchymal stem cells (MSCs), wherein the epithelial lung cells express at least one epithelial marker selected from the group consisting of CCSP, pro-SPC and cytokeratin-5.

Yet another aspect includes a method of alleviating or treating a lung defect in a mammal, the method comprising administering to the mammal a therapeutically effective amount of a population of lung cells produced by a method of differentiating a mesenchymal stem cell (MSC) into a lung cell wherein the method comprises culturing the MSCs on a substrate thereby differentiating the MSCs into a lung cell.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A-F depicts the results of FACS analysis of adherent, passage 2, hBM-MSC and hAT-MSC samples, which indicates that the cells express mesenchymal stromal cell markers and markers of epithelium. (FIG. 1A) Morphology of passage 2 hBM-MSCs. (FIG. 1B) hBM-MSCs are positive for MSC markers including CD90, CD105 and CD73, and they are CD45 negative. (FIG. 1C) A subpopulation of hBM-MSCs express the epithelial markers pro-SPC, CCSP and cytokeratin-5. (FIG. 1D) Morphology of passage 2 hAT-MSCs. (FIG. 1E) FACS analysis of hAT-MSCs confirm these cells are also positive for MSC markers including CD90, CD105 and CD73, and they are CD45 negative. (FIG. 1F) hAT-MSCs also contain a population of cells that are positive for pro-SPC, CCSP and cytokeratin 5. Isotype controls and experimental samples are shown.

FIG. 2A-H depicts the results of experiments investigating lung bioreactor cultures seeded with hBM-MSCs (FIG. 2A, 2B) DAPI staining is used to reveal nuclei in native (FIG. 2A) and absence of nuclei in decellularized lungs (Figure B). (FIG. 2C) H&E histological section of lungs seeded with hBM-MSCs and cultured for 7 days in SAGM. (FIG. 2D) Immunostaining for pro-SPC shows numerous cells that are positive for the type 2 pneumocyte marker. (FIG. 2E, 2F) There were no cells that were positive by immunostaining for the Clara cell marker, CCSP (FIG. 2E), while there were sparse cells that were cytokeratin-5 positive (FIG. 2F). (FIG. 2G, 2H) As an additional method to positively identify the hBM-MSC derived cells as type 2 pneumocytes, TEM analysis was performed. TEM analysis of native type 2 cells (FIG. 2E) (arrows indicate lamellar bodies; chevrons indicate secretory vesicles). (FIG. 2F) Lungs reseeded with hBM-MSCs contain cells that have both lamellar bodies (arrows) and secretory vesicles (arrowheads), both are characteristics of type 2 pneumocytes.

FIG. 3A-D depicts the results of experiments demonstrating that human adipose mesenchymal stromal cells (hAT-MSCs) give rise to type 2 pneumocyte-like cells, and to Clara-like cells that line the airways when cultured in the lung bioreactor. (FIG. 3A) hAT-MSCs robustly repopulate the lung matrix following seven days of culture in SAGM in the acellular rat lung bioreactor. H&E staining reveals the particular affinity for the cells to inhabit the lining of the airways (arrows). (FIG. 3B) The cells that line the airways (arrows) are positive for the Clara cell marker, CCSP. (FIG. 3C) The cells that are growing on the matrix are positive for pro-SPC. The inset shows the granular, cytoplasmic staining of the cells positive for pro-SPC. (FIG. 3D) There is no indication that the hAT-MSCs maintain cytokeratin-5 expression when grown on the decellularized matrix.

FIG. 4-G depicts the results of experiments demonstrating the RT-PCR analysis of day 3 and day 7 lung bioreactor cultures seeded with either hBM-MSCs or with hAT-MSCs. (FIG. 4A-C) hBM-MSCs have increased gene expression levels of distal epithelial genes including SPC, aquaporin-1 and caveolin-1 with increased time in the lung bioreactor culture. (FIG. 4D-F) Similarly, hAT-MSCs increase the expression of distal genes with longer culture periods. The fold change of the cells in the lung bioreactors are all compared with MSCs grown in tissue culture flasks. (FIG. 4G) Primers used to amplify gene sequences.

FIG. 5A-E depicts the results of experiments demonstrating that hAT-MSCs and hBM-MSCs grown in SAGM actively produce surfactant. RT-PCR analysis of hBM-MSCs (FIG. 5A) and hAT-MSCs (FIG. 5B) seeded on an acellular rat lung indicates a progressive increase in SPC expression with time in culture. hBM-MSCs (FIG. 5D) and hAT-MSCs (FIG. 5E) cultured in SAGM for 7 days in a lung slice has visible surfactant droplets in the culture medium adjacent to the lung slice. (FIG. 5C) ELISA of the media samples indicates that at day 3, 5.5 ng/mL of SPC is present in the hAT-MSC lung slice cultures, and 3.3 ng/ml is present in the hBM-MSC cultures. At day 7, the concentration of SPC is lower at 1.1 ng/mL for hAT-MSC and 0.26 ng/mL for the hBM-MSC. All ELISA values were normalized to SAGM medium alone. Bars represent S.E.M.

FIG. 6A-F is a series of images demonstrating that substrate coatings influence epithelial marker expression in hBM-MSCs and hAT-MSCs. hBM-MSCs and hAT-MSCs were cultured on various ECM coatings (human ECM, laminin, fibronectin, collagen IV, and collagen I) in SAGM media. After 7 days of culture the hBM-MSCs (FIG. 6A) and hAT-MSCs (FIG. 6B) were analyzed by FACS for expression of CCSP, pro-SPC, and cytokeratin 5. Both sources of MSCs varied in terms of epithelial marker expression when cultured on different surface coatings. (FIG. 6C, 6D) RT-PCR analysis was also performed for expression of CCSP, SPC, and cytokeratin 5 after culture on the different surface coatings. The RT-PCR data coincide well with the FACS analysis and indicate that the highest expression of SPC is found in MSCs grown in human ECM compared with MSCs grown on other surface coatings. Also evident from these experiments were differences in cell morphology between hBM-MSCs (FIG. 6E) and hAT-MSCs (FIG. 6F) grown on human ECM.

FIG. 7A-F depicts the results of experiments demonstrating that rat lung bioreactor cultures seeded with hBM-MSCs and grown in 10% FBS/DMEM have adhered cells that have fibroblastic morphology and protein expression. (FIG. 7A) H&E histology of the 7 day cultures demonstrates the presence of cells spread uniformly throughout the recellularized organ. The attached cells are largely fibroblastic in morphology. (FIG. 7B) Immunofluorescence for a-sma, a marker used to detect myofibroblasts, reveals that most of the cells are positive for the myofibroblast marker. (FIG. 7C, 7D) Immunofluorescence analysis of CCSP expression in cytospins of hBM-MSCs that were grown in either 10% FBS/DMEM or small airway growth medium (SAGM). CCSP expression is maintained in cells cultured in either condition. (FIG. 7E, 7F) Immunofluorescence for a-sma expression in cells grown in either medium shows that a-sma is mostly absent when the cells are grown in SAGM.

FIG. 8A-D depicts the results of experiments demonstrating that there is no visible surfactant secretion present in lung slices reseeded with either hAT-MSC or hBM-MSC and cultured in 10% FBS/DMEM. (FIG. 8A) hAT-MSCs and (FIG. 8B) hBM-MSCs cultured on lung slices in 10% FBS/DMEM do not contain visible surfactant in the media. (FIG. 8C, 8D) As a control, unseeded samples were also analyzed for surfactant pools in the medium but these did not contain any visible surfactant.

FIG. 11A-J depicts the results of experiments demonstrating that hBM-MSCs cultured on a decellularized liver matrix, are morphologically different than those cultured on lung. (FIG. 11A) Whole-mount image of a decellularized liver. (FIG. 11B) H&E histology of the decellularized liver shows that there are no remaining cells on the matrix. (FIG. 11C, 11D) Reseeded liver slices were cultured in 10% FBS/DMEM (FIG. 11C) or in SAGM (FIG. 11D) for 3 days. Morphological comparison between these cells and those seeded on the lung (FIG. 3C) indicates a large difference in cell shape. Cells grown in either 10% FBS/DMEM or in SAGM were negative for CCSP and cytokeratin 5 (FIG. 11E, 11G, 11H, 11J), whereas few cells remained positive for pro-SPC (FIG. 11F, 11I).

DETAILED DESCRIPTION

Figure 1C:
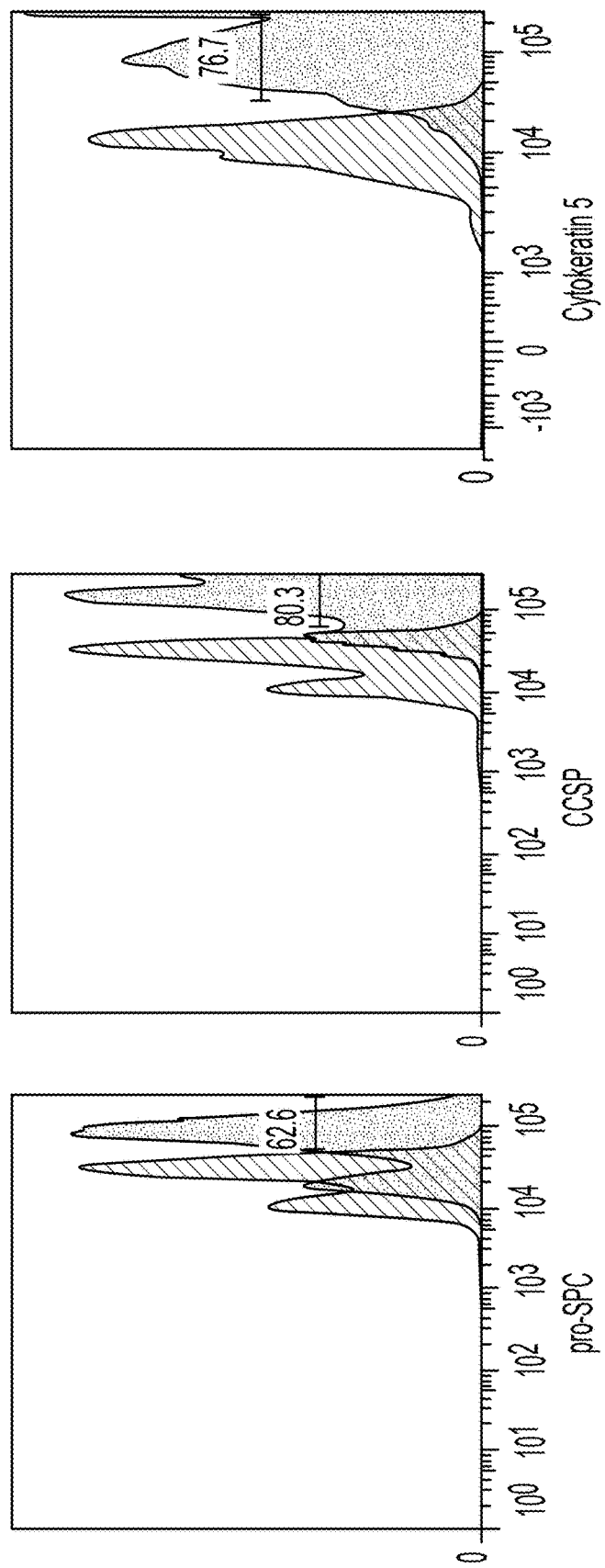

The invention is based on the discovery that human bone marrow and adipose derived mesenchymal stromal cells (hBM-MSCs, and hAT-MSCs, respectively) undergo changes in lung epithelial marker expression depending on the substrate (e.g., decellularized lung tissue or culture plates containing different surface coatings) on which they are cultured.

In one embodiment, hBM-MSCs, when cultured on decellularized lung tissue, attach to the decellularized lung matrix, particularly to distal lung regions and express markers associated with type 2 pneumocytes (pro-SPC), contain lamellar bodies, and actively secrete surfactant protein C. hBM-MSCs also differentiate into cells that are positive for cytokeratin-5, but are negative for other lung associated markers such as CCSP.

In one embodiment, hAT-MSCs, when cultured on decellularized lung tissue exhibited type 2 pneumocyte-like cell characteristics, as well as Clara-like cell characteristics. In contrast to hBM-MSCs, hAT-MSC give rise to Clara-like cells (e.g., positive for CCSP) that line the airways in anatomically correct positions. In addition, hAT-MSCs, in contrast to hBM-MSCs do not give rise to cytokeratin-5 positive cells.

Accordingly, the invention is based on the discovery that the capacity for MSCs to differentiate towards lung epithelial phenotypes is dependent on substrate, tissue of origin and culture media.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well-known and commonly employed in the art.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent based on the context in which it is used.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, fat, cardiac muscle, and the like. Each of these stem cells can be characterized based on gene expression, factor responsiveness, and morphology in culture. Exemplary adult stem cells include neural stem cells, neural crest stem cells, mesenchymal stem cells, hematopoietic stem cells, and pancreatic stem cells. As indicated above, stem cells have been found resident in virtually every tissue. Accordingly, the present invention appreciates that stem cell populations can be isolated from virtually any animal tissue.

As used herein, "autologous" refers to a biological material derived from the same individual into whom the material will later be re-introduced.

As used herein, "allogeneic" refers to a biological material derived from a genetically different individual of the same species as the individual into whom the material will be introduced.

As used herein, to "alleviate" a disease, defect, disorder or condition means reducing the severity of one or more symptoms of the disease, defect, disorder or condition.

As used herein, the term "basal medium" refers to a solution of amino acids, vitamins, salts, and nutrients that is effective to support the growth of cells in culture, although normally these compounds will not support cell growth unless supplemented with additional compounds. The nutrients include a carbon source (e.g., a sugar such as glucose) that can be metabolized by the cells, as well as other compounds necessary for the cells' survival. These are compounds that the cells themselves cannot synthesize, due to the absence of one or more of the gene(s) that encode the protein(s) necessary to synthesize the compound (e.g., essential amino acids) or, with respect to compounds which the cells can synthesize, because of their particular developmental state the gene(s) encoding the necessary biosynthetic proteins are not being expressed as sufficient levels. A number of base media are known in the art of mammalian cell culture, such as Dulbecco's Modified Eagle Media (DMEM), Knockout-DMEM (KO-DMEM), and DMEM/F12, although any base medium that supports the growth of primate embryonic stem cells in a substantially undifferentiated state can be employed.

As used here, "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

As used herein, the term "biocompatible lattice," is meant to refer to a substrate that can facilitate formation into three-dimensional structures conducive for tissue development. Thus, for example, cells can be cultured or seeded onto such a biocompatible lattice, such as one that includes extracellular matrix material, synthetic polymers, cytokines, growth factors, etc. The lattice can be molded into desired shapes for facilitating the development of tissue types. Also, at least at an early stage during culturing of the cells, the medium and/or substrate is supplemented with factors (e.g., growth factors, cytokines, extracellular matrix material, etc.) that facilitate the development of appropriate tissue types and structures.

"Bioactive agents," as used herein, can include one or more of the following: chemotactic agents; therapeutic agents (e.g., antibiotics, steroidal and non-steroidal analgesics and anti-inflammatories (including certain amino acids such as glycine), anti-rejection agents such as immunosuppressants and anti-cancer drugs); various proteins (e.g., short term peptides, bone morphogenic proteins, collagen, hyaluronic acid, glycoproteins, and lipoprotein); cell attachment mediators; biologically active ligands; integrin binding sequence; ligands; various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin derived growth factor (e.g., IGF-1, IGF-II) and transforming growth factors (e.g., TGFβ I-III) parathyroid hormone, parathyroid hormone related peptide, bone morphogenic proteins (e.g., BMP-2, BMP-4; BMP-6; BMP-7; BMP-12; BMP-13; BMP-14), sonic hedgehog, growth differentiation factors (e.g., GDF5, GDF6, GDF8), recombinant human growth factors (e.g., MP52, and MP-52 variant rhGDF-5), cartilage-derived morphogenic proteins (CDMP-1; CDMP-2, CDMP-3)); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate. Suitable effectors likewise include the agonists and antagonists of the agents described above. The growth factor can also include combinations of the growth factors described above. In addition, the growth factor can be autologous growth factor that is supplied by platelets in the blood. In this case, the growth factor from platelets will be an undefined cocktail of various growth factors. If other such substances have therapeutic value in the orthopedic field, it is anticipated that at least some of these substances will have use in the present invention, and such substances should be included in the meaning of "bioactive agent" and "bioactive agents" unless expressly limited otherwise. Preferred examples of bioactive agents include culture media, bone morphogenic proteins, growth factors, growth differentiation factors, recombinant human growth factors, cartilage-derived morphogenic proteins, hydrogels, polymers, antibiotics, anti-inflammatory medications, immunosuppressive mediations, autologous, allogenic or xenologous cells such as stem cells, chondrocytes, fibroblast and proteins such as collagen and hyaluronic acid. Bioactive agents can be autologous, allogenic, xenogenic or recombinant.

The term "biologically compatible carrier" or "biologically compatible medium" refers to reagents, cells, compounds, materials, compositions, and/or dosage formulations which are suitable for use in contact with the tissues of human beings and animals without excessive toxicity, irritation, allergic response, or other complication commensurate with a reasonable benefit/risk ratio.

The terms "cells" and "population of cells" are used interchangeably and refer to a plurality of cells, i.e., more than one cell. The population may be a pure population comprising one cell type. Alternatively, the population may comprise more than one cell type. In the present invention, there is no limit on the number of cell types that a cell population may comprise.

The term "cell medium" as used herein, refers to a medium useful for culturing cells. An example of a cell medium is a medium comprising DMEM/F 12 Ham's, 10% fetal bovine serum, 100 U penicillin/100 μg streptomycin/0.25 μg Fungizone. Typically, the cell medium comprises a base medium, serum and an antibiotic/antimycotic. However, cells can be cultured with stromal cell medium without an antibiotic/antimycotic and supplemented with at least one growth factor. Preferably the growth factor is human epidermal growth factor (hEGF). The preferred concentration of hEGF is about 1-50 ng/ml, more preferably the concentration is about 5 ng/ml. The preferred base medium is DMEM/F12 (1:1). The preferred serum is fetal bovine serum (FBS) but other sera may be used including horse serum or human serum. Preferably up to 20% FBS will be added to the above media in order to support the growth of stromal cells. However, a defined medium could be used if the necessary growth factors, cytokines, and hormones in FBS for cell growth are identified and provided at appropriate concentrations in the growth medium. It is further recognized that additional components may be added to the culture medium. Such components include but are not limited to antibiotics, antimycotics, albumin, growth factors, amino acids, and other components known to the art for the culture of cells. Antibiotics which can be added into the medium include, but are not limited to, penicillin and streptomycin. The concentration of penicillin in the culture medium is about 10 to about 200 units per ml. The concentration of streptomycin in the culture medium is about 10 to about 200 µg/ml. However, the invention should in no way be construed to be limited to any one medium for culturing cells. Rather, any media capable of supporting cells in tissue culture may be used.

The term "decellularized" or "decellularization" as used herein refers to a biostructure (e.g., an organ, or part of an organ), from which the cellular and tissue content has been removed leaving behind an intact acellular infra-structure. Organs such as the kidney are composed of various specialized tissues. The specialized tissue structures of an organ, or parenchyma, provide the specific function associated with the organ. The supporting fibrous network of the organ is the stroma. Most organs have a stromal framework composed of unspecialized connecting tissue which supports the specialized tissue. The process of decellularization removes the specialized tissue, leaving behind the complex three-dimensional network of connective tissue. The connective tissue infra-structure is primarily composed of collagen. The decellularized structure provides a biocompatible substrate onto which different cell populations can be infused. Decellularized biostructures can be rigid, or semi-rigid, having an ability to alter their shapes. Examples of decellularized organs useful in the present invention include, but are not limited to, the heart, lung, kidney, liver, pancreas, spleen, bladder, ureter and urethra, cartilage, bone, brain, spine cord, peripheral nerve.

The term "dedifferentiation", as used herein, refers to the return of a cell to a less specialized state. After dedifferentiation, such a cell will have the capacity to differentiate into more or different cell types than was possible prior to re-programming. The process of reverse differentiation (i.e., de-differentiation) is likely more complicated than differentiation and requires "re-programming" the cell to become more primitive.

The term "differentiated cell" is meant any primary cell that is not, in its native form, pluripotent as that term is defined herein. Stated another way, the term "differentiated cell" refers to a cell of a more specialized cell type derived from a cell of a less specialized cell type (e.g., a stem cell such as an induced pluripotent stem cell) in a cellular differentiation process. Without wishing to be limited to theory, a pluripotent stem cell in the course of normal ontogeny can differentiate first to an endoderm cell that is capable of forming lung cells and other endoderm cell types. Endoderm cells can also be differentiate into other cells of endodermal origin, e.g. lung, liver, intestine, thymus etc.

"Differentiation medium" is used herein to refer to a cell growth medium comprising an additive or a lack of an additive such that a stem cell, fetal pulmonary cell or other such progenitor cell, that is not fully differentiated, develops into a cell with some or all of the characteristics of a differentiated cell when incubated in the medium.

The term "embryonic stem cell" is used to refer to the pluripotent stem cells of the inner cell mass of the embryonic blastocyst (see U.S. Pat. Nos. 5,843,780, 6,200,806). Such cells can similarly be obtained from the inner cell mass of blastocysts derived from somatic cell nuclear transfer (see, for example, U.S. Pat. Nos. 5,945,577, 5,994,619, 6,235,970). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

As used herein, "epithelial cell" means a cell which forms the outer surface of the body and lines organs, cavities and mucosal surfaces.

As used herein, "endothelial cell" means a cell which lines the blood and lymphatic vessels and various other body cavities.

As used herein "endogenous" refers to any material from or produced inside an organism, cell or system.

"Exogenous" refers to any material introduced into or produced outside an organism, cell, or system.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "endoderm cell" as used herein refers to a cell which is from one of the three primary germ cell layers in the very early embryo (the other two germ cell layers are the mesoderm and ectoderm). The endoderm is the innermost of the three layers. An endoderm cell differentiates to give rise first to the embryonic gut and then to the linings of respiratory and digestive tracts (e.g. the intestine), the liver and the pancreas.

"Expandability" is used herein to refer to the capacity of a cell to proliferate, for example, to expand in number or, in the case of a population of cells, to undergo population doublings.

As used herein, "extracellular matrix composition" includes both soluble and non-soluble fractions or any portion thereof. The non-soluble fraction includes those secreted ECM proteins and biological components that are deposited on the support or scaffold. The soluble fraction includes refers to culture media in which cells have been cultured and into which the cells have secreted active agent(s) and includes those proteins and biological components not deposited on the scaffold. Both fractions may be collected, and optionally further processed, and used individually or in combination in a variety of applications as described herein.

"Fibrosis" is the formation or development of excess fibrous connective tissue in an organ or tissue as a reparative or reactive process, as opposed to a formation of fibrous tissue as a normal constituent of an organ or tissue. Pulmonary fibrosis is a severe chronic disease characterized by a loss of elasticity and lung epithelial cells, replaced by interstitial myofibroblasts and deposition of extracellular matrix proteins in the lung interstitium leading to pulmonary structural remodeling.

As used herein, a "graft" refers to a cell, tissue or organ that is implanted into an individual, typically to replace, correct or otherwise overcome a defect. A graft may further comprise a scaffold. The tissue or organ may consist of cells that originate from the same individual; this graft is referred to herein by the following interchangeable terms: "autograft," "autologous transplant," "autologous implant" and "autologous graft." A graft comprising cells from a genetically different individual of the same species is referred to herein by the following interchangeable terms: "allograft", "allogeneic transplant," "allogeneic implant" and "allogeneic graft." A graft from an individual to his identical twin is referred to herein as an "isograft", a "syngeneic transplant", a "syngeneic implant" or a "syngeneic graft." A "xenograft," "xenogeneic transplant" or "xenogeneic implant" refers to a graft from one individual to another of a different species.

As used herein, the term "growth factor product" refers to a protein, peptide, mitogen, or other molecule having a growth, proliferative, differentiative, or trophic effect on a cell. Growth factors include, but are not limited to, fibroblast growth factor (FGF), basic fibroblast growth factor (bFGF), acidic fibroblast growth factor (aFGF), epidermal growth factor (EGF), insulin-like growth factor-I (IGF-T), insulin-like growth factor-II (IGF-II), platelet-derived growth factor (PDGF), vascular endothelial cell growth factor (VEGF), activin-A, bone morphogenic proteins (BMPs), insulin, growth hormone, erythropoietin, thrombopoietin, interleukin 3 (IL-3), interleukin 6 (IL-6), interleukin 7 (IL-7), macrophage colony stimulating factor, c-kit ligand/stem cell factor, osteoprotegerin ligand, insulin, nerve growth factor, ciliary neurotrophic factor, cytokines, chemokines, morphogens, neutralizing antibodies, other proteins, and small molecules. Preferably, the FGF is selected from the group selected from FGF2, FGF7, FGF10, and any combination thereof.

As used herein, the term "growth medium" is meant to refer to a culture medium that promotes growth of cells. A growth medium will generally contain animal serum. In some instances, the growth medium may not contain animal serum.

An "isolated cell" refers to a cell which has been separated from other components and/or cells which naturally accompany the isolated cell in a tissue or mammal.

An "isolated nucleic acid" refers to a nucleic acid segment or fragment which has been separated from sequences which flank it in a naturally-occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

The term "lung specific" refers to a nucleic acid molecule or polypeptide that is expressed predominantly in the lung as compared to other tissues in the body. In a preferred embodiment, a "lung specific" nucleic acid molecule or polypeptide is expressed at a level that is 5-fold higher than any other tissue in the body. In a more preferred embodiment, the "lung specific" nucleic acid molecule or polypeptide is expressed at a level that is 10-fold higher than any other tissue in the body, more preferably at least 15-fold, 20-fold, 25-fold, 50-fold or 100-fold higher than any other tissue in the body. Nucleic acid molecule levels may be measured by nucleic acid hybridization, such as Northern blot hybridization, or quantitative PCR. Polypeptide levels may be measured by any method known to accurately measure protein levels, such as Western blot analysis.

"Lung tissue" can include, but is not limited to, all lung tissue structures and associated tissues, including, but not limited to, veins, arteries, vessels, capillaries, and cells of the type that are part of, or associated with, such structures; lung and pleural tissue; and vascular smooth muscle, pericyte, and vascular endothelial lineages and/or phenotypes.

The terms "precursor cell," "progenitor cell," and "stem cell" are used interchangeably in the art and as used herein refer either to a pluripotent or lineage-uncommitted progenitor cell, which is potentially capable of an unlimited number of mitotic divisions to either renew itself or to produce progeny cells which will differentiate into the desired cell type. In contrast to pluripotent stem cells, lineage-committed progenitor cells are generally considered to be incapable of giving rise to numerous cell types that phenotypically differ from each other. Instead, progenitor cells give rise to one or possibly two lineage-committed cell types.

"Proliferation" is used herein to refer to the reproduction or multiplication of similar forms, especially of cells. That is, proliferation encompasses production of a greater number of cells, and can be measured by, among other things, simply counting the numbers of cells, measuring incorporation of $^3$H-thymidine into the cell, and the like.

"Progression of or through the cell cycle" is used herein to refer to the process by which a cell prepares for and/or enters mitosis and/or meiosis. Progression through the cell cycle includes progression through the G1 phase, the S phase, the G2 phase, and the M-phase.

As used herein, "scaffold" refers to a structure, comprising a biocompatible material, that provides a surface suitable for adherence and proliferation of cells. A scaffold may further provide mechanical stability and support. A scaffold may be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

As used herein, the phrase "small airway growth medium" or "SAGM" refers to a growth medium that comprises one or more of the following components, hydrocortisone, epidermal growth factor, epinephrine, transferring, insulin, retinoic acid, triiodothyronine, and bovine serum albumin-fatty acid free.

As used herein, the phrase "stem cells" refers both to the earliest renewable cell population responsible for generating cell mass in a tissue or body and the very early progenitor cells, which are somewhat more differentiated, yet are not committed and can readily revert to become a part of the earliest renewable cell population.

As used herein, a "substantially purified" cell is a cell that is essentially free of other cell types. Thus, a substantially purified cell refers to a cell which has been purified from other cell types with which it is normally associated in its naturally-occurring state.

As used herein, the terms "subject" and "patient" are used interchangeably. As used herein, a subject is preferably a mammal such as a non-primate (e.g., cows, pigs, horses, cats, dogs, rats, etc.) and a primate (e.g., monkey and human), most preferably a human.

As used herein, to "treat" means reducing the frequency with which symptoms of a disease, defect, disorder, or adverse condition, and the like, are experienced by a patient.

As used herein, a "therapeutically effective amount" is the amount of a composition of the invention sufficient to provide a beneficial effect to the individual to whom the composition is administered.

As used herein, "tissue engineering" refers to the process of generating tissues ex vivo for use in tissue replacement or reconstruction. Tissue engineering is an example of "regenerative medicine," which encompasses approaches to the repair or replacement of tissues and organs by incorporation of cells, gene or other biological building blocks, along with bioengineered materials and technologies.

As used herein, the terms "tissue grafting" and "tissue reconstructing" both refer to implanting a graft into an individual to treat or alleviate a tissue defect, such as a lung defect or a soft tissue defect.

"Transplant" refers to a biocompatible lattice or a donor tissue, organ or cell, to be transplanted. An example of a transplant may include but is not limited to skin cells or tissue, bone marrow, and solid organs such as heart, pancreas, kidney, lung and liver.

Generally, a "trophic factor" is defined as a substance that promotes survival, growth, proliferation and/or maturation of a cell, or stimulates increased activity of a cell.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to the discovery that different stem cell types (e.g., bone marrow-derived mesenchymal stem cells (BM-MSC) and adipose-derived mesenchymal stem cells (AT-MSC)) undergo large changes in lung epithelial marker expression depending on the substrate on which they are cultured. An example of a substrate includes but is not limited to a decellularized lung tissue and a culture plate containing different surface coatings. Teachings of a decellularized lung tissue can be found in U.S. Patent Application Publication Number 20120064050, the content of which is hereby incorporated by reference.

In one embodiment, BM-MSCs, when placed onto decellularized lung, are capable of expressing the type 2 pneumocyte marker pro-SPC as well as the proximal airway marker cytokeratin-5. In one embodiment, BM-MSC can take on the phenotype of type II alveolar epithelial cells (also referred to as type 2 pneumocytes), when expanded and cultured under suitable conditions. In another embodiment, when expanded and cultured under suitable conditions, BM-MSCs exhibit cytoplasmic structures associated with function that is similar to that contained within native type 2 cells.

In another embodiment, AT-MSCs give rise to pro-SPC positive cells. In another embodiment, when expanded and cultured under suitable conditions, AT-MSC give rise to Clara-like cells (e.g., positive for CCSP) that line the airways in anatomically correct positions. This is in contrast to BM-MSCs, which do not maintain expression of CCSP nor adhere to the airways. In another embodiment, in contrast to BM-MSCs, AT-MSCs do not give rise to cytokeratin-5 positive cells.

Accordingly, the invention provides compositions and methods of generating a desired cell type. Therefore, the cells of the invention serve as a promising source of cells for use therapeutically to treat distal lung diseases, lung injuries, and genetic diseases that affect the lung.

The present invention provides a method of differentiating BM-MSCs into cells that exhibit the type 2 pneumocyte marker pro-SPC as well as the proximal airway marker cytokeratin-5. In one embodiment, the present invention provides a method of differentiating BM-MSCs to exhibit at least one phenotype of type II alveolar epithelial cells. In another embodiment, the present invention provides a method of differentiating BM-MSCs to exhibit cytoplasmic structures associated with function that is similar to that contained within native type 2 cells.

Accordingly, the invention provides a method for directed differentiation of BM-MSCs into cell types and tissues associated with type II alveolar epithelial cells.

The present invention provides a method of differentiating AT-MSCs into cells that exhibit the type 2 pneumocyte marker pro-SPC but do not give rise to cytokeratin-5 positive cells. In one embodiment, the present invention provides a method of differentiating AT-MSCs to cells that are positive for CCSP, a marker of Clara cells. In another the present invention provides a method of differentiating AT-MSCs to give rise to Clara-like cells (e.g., positive for CCSP) that line the airways in anatomically correct positions.

Accordingly, the invention provides a method for directed differentiation of AT-MSCs into cell types and tissues associated with Clara cells.

Culturing Conditions

The invention relates to the use of any cell to differentiate into a type of lung cell (e.g., type II alveolar epithelial cells or Clara cells). Preferably, the suitable cell or cells are regenerative. An example of a regenerative cell includes, but is not limited to, a stem cell, an embryonic stem cell, an adult stem cell, an umbilical cord blood cell, a tissue-derived stem or progenitor cell, a bone marrow-derived stem or progenitor cell, a blood-derived stem or progenitor cell, an adipose-derived stem or progenitor cell, a mesenchymal stem cell (MSC), a skeletal muscle-derived cells, a multipotent adult progenitor cell (MAPC), a fetal pulmonary cell, differentiated pulmonary epithelial cells, pulmonary progenitor cells, vascular progenitor cells, differentiated vascular cells and the like. Additional regenerative cells that can be used include bone marrow-derived stem cells such as bone marrow mononuclear cells (BM-MNC), endothelial or vascular stem or progenitor cells, and peripheral blood-derived stem cells such as endothelial progenitor cells (EPC).

Preferably, the suitable cell is isolated from a mammal, more preferably a primate and more preferably still, a human. The cells useful in the methods of the present invention are isolated using methods discussed herein, for example in the Examples section, or by any method known in the art. Following isolation, the suitable cells are cultured in a culture medium.

Culture medium compositions typically include essential amino acids, salts, vitamins, minerals, trace metals, sugars, lipids and nucleosides. Cell culture medium attempts to supply the components necessary to meet the nutritional needs required to grow cells in a controlled, artificial and in vitro environment. Nutrient formulations, pH, and osmolarity vary in accordance with parameters such as cell type, cell density, and the culture system employed. Many cell culture medium formulations are documented in the literature and a number of media are commercially available.

Once the culture medium is incubated with cells, it is known to those skilled in the art as "conditioned medium." Conditioned medium contains many of the original components of the medium, as well as a variety of cellular metabolites and secreted proteins, including, for example, biologically active growth factors, inflammatory mediators and other extracellular proteins.

A skilled artisan will recognize that the culturing conditions can be modified to the suitable cell. Media formulations that support the growth of an MSC include, but are not limited to, Minimum Essential Medium Eagle, ADC-1, LPM (bovine serum albumin-free), F10 (HAM), F12 (HAM), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM-without serum), Yamane, IMEM-20, Glasgow Modification Eagle Medium (GMEM), Leibovitz L-15 Medium, McCoy's 5A Medium, Medium M199 (M199E—with Earle's salt base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with nonessential amino acids), and the like.

Additional non-limiting examples of media useful in the methods of the invention may contain fetal serum of bovine or other species at a concentration at least 1% to about 30%, preferably at least about 5% to 15%, most preferably about 10%. Embryonic extract of bovine or other species can be present at a concentration of about 1% to 30%, preferably at least about 5% to 15%, most preferably about 10%.

Typically, the culture medium comprises a base medium, serum and an antibiotic/antimycotic. One preferred base medium is DMEM/F12 (1:1). The preferred serum is fetal bovine serum (FBS) but other sera may be used, including horse serum or human serum. Preferably up to 20% FBS will be added to the above medium in order to support the growth of MSCs. However, a defined medium can be used if the necessary growth factors, cytokines, and hormones in FBS for MSC growth are identified and provided at appropriate concentrations in the growth medium. It is further recognized that additional components may be added to the culture medium. Such components include, but are not limited to, antibiotics, antimycotics, albumin, growth factors, amino acids, and other components known to the art for the culture of cells. Antibiotics which can be added into the medium include, but are not limited to, penicillin and streptomycin. The concentration of penicillin in the culture medium is about 10 to about 200 units per ml. The concentration of streptomycin in the culture medium is about 10 to about 200 µg/ml. However, the invention should in no way be construed to be limited to any one medium for culturing NPCs. Rather, any media capable of supporting pulmonary cells in tissue culture may be used.

Other ingredients often used in media formulations include fat soluble vitamins (including A, D, E and K) steroids and their derivatives, cholesterol, fatty acids and lipids Tween 80, 2-mercaptoethanol pyramidines as well as a variety of supplements including serum (fetal, horse, calf, etc.), proteins (insulin, transferrin, growth factors, hormones, etc.) antibiotics (gentamicin, penicillin, streptomycin, amphotericin B, etc.) whole egg ultra filtrate, and attachment factors (fibronectins, vitronectins, collagens, laminins, tenascins, etc.).

The media may or may not need to be supplemented with growth factors and other proteins such as attachment factors since many of the cell constructs, particularly the three-dimensional cell and tissue culture constructs described in this application themselves elaborate such growth and attachment factors and other products into the media.

Soluble factors refer to factors released and present in culture media of stem cells. Examples of soluble factors include but are not limited to vascular endothelial growth factor (VEGF), insulin growth factor (IGF), hepatocyte growth factor (HGF), keratinocyte growth factor (KGF) and other members of the fibroblast growth factor family.

Following isolation, MSCs may be incubated in culture medium, in a culture apparatus for a period of time or until the cells reach confluency before passing the cells to another culture apparatus. Following the initial plating, the cells can be maintained in culture for a period of about 6 days to yield the Passage 0 (P0) population. The cells may be passaged for an indefinite number of times, each passage comprising culturing the cells for about 6-7 days, during which time the cell doubling time can range between about 3 to about 5 days. The culturing apparatus can be of any culture apparatus commonly used in culturing cells in vitro.

MSCs described herein may be cryopreserved according to routine procedures. Preferably, about one to ten million cells are cryopreserved in culture medium containing 10% DMSO in vapor phase of liquid N2. Frozen cells may be thawed by swirling in a 37° C. bath, resuspended in fresh growth medium, and expanded as described above.

The invention also provides cells that "seed" the scaffold. MSCs can be cultured on the scaffold. The cells can also differentiate in vitro by culturing the cells in differentiation medium. Alternatively, the cells can differentiate in vivo when they establish contact with a tissue within the mammal or when the cells are sufficiently close to a tissue to be influenced by substances (e.g., growth factors, enzymes, or hormones) released from the tissue. In other words, MSCs of the matrix can establish contact with a tissue, such as lung, by virtue of receiving signals from the tissue. Such signaling would occur, for example, when a receptor on the surface of an MSC, or on the surface of a cell descended from a MSC, binds and transduces a signal from a molecule such as a growth factor, enzyme, or hormone that was released by a tissue within the mammal. These agents guide differentiation so that the MSCs come to express some and possibly most (if not all) of the same proteins normally expressed by differentiated cells in the tissue in which they have been placed.

Alternatively, or in addition, MSCs of the matrix can be induced to differentiate by adding a substance (e.g., a growth factor, enzyme, hormone, or other signaling molecule) to the cell's environment. For example, a substance can be added to the biological scaffolding of the invention.

In another embodiment, the present invention provides a method of culturing cells of the invention in the presence of ECM proteins on a surface (e.g., two-dimensional or three-dimensional) in a suitable growth medium. In one embodiment, the ECM is coated on the surface of a culturing apparatus.

In another embodiment, the present invention includes a tissue culture system. In various aspects, the culture system is composed of the ECM compositions described herein, such as being included in two-dimensional or three-dimensional support materials. In another aspect, the ECM compositions described herein serve as a support or two-dimensional or three-dimensional support for the growth of various cell types. For example, the culture system can be used to support the growth of the cells of the invention. In one aspect, the culture system can be used to support the differentiation of the cells.

ECM is known to be secreted by certain cells and is comprised mainly of fibrous proteins, polysaccharides, and other minor constituents. Its components include structural elements such as collagen and elastin, adhesive proteins such as the glycoproteins fibronectin, laminin, vitronectin, thrombospondin I and tenascins, as well as proteoglycans such as decorin, biglycan, chondroitin sulfate and heparin sulfate and glycosaminoglycans (GAG) such as hyaluronic acid (HA).

In one embodiment, the ECM compositions can include any or all of the following: fibronectin, fibrillin, laminin, elastin, members of the collagen family (e.g., collagen I, III, and IV), glycosaminoglycans, ground substance, reticular fibers and thrombospondin. Preferably, human ECM is used for culturing the definitive endoderm. In one embodiment, human ECM includes collagens, laminin, fibronectin, tenascin, elastin, and a number of proteoglycans and glycosaminoglycans.

In another embodiment, it is desirable to culture the cells on a solid support that comprises a reconstituted basement membrane, wherein the membrane can be obtained by being extracted and prepared from a suitable cell tissue that is contained in the thin, membranous extracellular matrix present below the cell layer in vivo and contains proteins and glycoproteins such as laminin, collagen IV and heparin sulphate proteoglycan as well as various cell growth factors and activating factors, etc.

In one embodiment, the predominant major extracellular matrix component is fibrillar collagen, particularly collagen type I. However, other fibrillar and non-fibrillar collagens, including collagen types II, III, IV, V, VI, VII, VIII, IX, X, XI, XII, XIII, XIV, XV, XVI, XVII, XVIII, XIX, and others.

The ECM compositions of the present invention may be processed in a variety of ways. Accordingly, in one embodiment, the present invention includes a tissue culture system. In various aspects, the culture system is composed of the ECM compositions described herein. The ECM compositions of the present invention may be incorporated into the tissue culture system in a variety of ways. For example, compositions may be incorporated as coatings, by impregnating three-dimensional scaffold materials as described herein, or as additives to media for culturing cells. Accordingly, in one aspect, the culture system can include three-dimensional support materials impregnated with any of the ECM compositions described herein, such as growth factors or embryonic proteins.

While MSCs and associated cellular matrix can eventually become fully differentiated, and while this is desirable in some circumstances (e.g., where the cells are used to recreate a histologically mature and complete tissue), not all of the cells administered need to be fully differentiated to achieve successful treatment; MSCs of the cellular matrix need only differentiate to a point sufficient to treat the mammal. That point can be reached either before or after the matrix is administered to the patient.

Differentiation occurs when a cell of the matrix expresses essentially the same phenotype as a mature cell at the site of implantation. For example, for the purpose of defining this invention, a MSC of a cellular matrix, having been implanted into the lung, is differentiated when it expresses essentially the same proteins expressed by the lung, e.g., an alveolar epithelial cell. Antibodies to lung markers are commercially available or otherwise readily attainable.

Differentiated cells can also be identified by their gross morphology and by the connections they form with other cells. For example, cells that differentiate into lung cells can develop complex morphology resembling bronchioles. For example, the invention is based on the novel discovery that different MSC type (e.g., bone marrow-derived mesenchymal stem cells (BM-MSC) and adipose-derived mesenchymal stem cells (AT-MSC)) undergo large changes in lung epithelial marker expression depending on the culture conditions, include substrates or scaffold, on which they are cultured. For example, BM-MSCs differentiate into cell types and tissues associated with type II alveolar epithelial cells. Whereas AT-MSCs differentiate into cell types and tissues associated with Clara cells.

The number of cells that is introduced into and onto a decellularized organ in order to generate an organ or tissue is dependent on both the organ (e.g., which organ, the size and weight of the organ) or tissue and the type and developmental stage of the regenerative cells. Different types of cells may have different tendencies as to the population density those cells will reach. Similarly, different organ or tissues may be cellularized at different densities. By way of example, a decellularized organ or tissue can be seeded with at least about 1,000 (e.g., at least 10,000, 100,000, 1,000, 000, 10,000,000, or 100,000,000) regenerative cells; or can have from about 1,000 cells/mg tissue (wet weight, i.e., prior to decellularization) to about 10,000,000 cells/mg tissue (wet weight) attached thereto.

Cells can be introduced to a decellularized organ or tissue by injection into one or more locations. In addition, more than one type of cell (i.e., a cocktail of cells) can be introduced into a decellularized organ or tissue. For example, a cocktail of cells can be injected at multiple positions in a decellularized organ or tissue or different cell types can be injected into different portions of a decellularized organ or tissue. Alternatively, or in addition to injection, regenerative cells or a cocktail of cells can be introduced by perfusion into a cannulated decellularized organ or tissue. For example, cells can be perfused into a decellularized organ using a perfusion medium, which can then be changed to an expansion and/or differentiation medium to induce growth and/or differentiation of the regenerative cells. In the case of a lung tissue, the cells can be introduced into either or both of the airway compartment via the trachea, or the vascular compartment via the pulmonary artery or vein.

During recellularization, an organ or tissue is maintained under conditions in which at least some of the regenerative cells can multiply and/or differentiate within and on the decellularized organ or tissue. Those conditions include, without limitation, the appropriate temperature and/or pressure, electrical and/or mechanical activity, force, the appropriate amounts of $O_2$ and/or $CO_2$, an appropriate amount of humidity, and sterile or near-sterile conditions. During recellularization, the decellularized organ or tissue and the cells attached thereto are maintained in a suitable environment. For example, the cells may require a nutritional supplement (e.g., nutrients and/or a carbon source such as glucose), exogenous hormones or growth factors, and/or a particular pH.

Cells can be allogeneic to a decellularized organ or tissue (e.g., a human decellularized organ or tissue seeded with human cells), or regenerative cells can be xenogeneic to a decellularized organ or tissue (e.g., a pig decellularized organ or tissue seeded with human cells).

In some instances, an organ or tissue generated by the methods described herein is to be transplanted into a patient. In those cases, the cells used to recellularize a decellularized organ or tissue can be obtained from the patient such that the regenerative cells are autologous to the patient. Cells from a patient can be obtained from, for example, blood, bone marrow, tissues, or organs at different stages of life (e.g., prenatally, neonatally or perinatally, during adolescence, or as an adult) using methods known in the art. Alternatively, cells used to recellularize a decellularized organ or tissue can be syngeneic (i.e., from an identical twin) to the patient, cells can be human lymphocyte antigen (HLA)-matched cells from, for example, a relative of the patient or an HLA-matched individual unrelated to the patient, or cells can be allogeneic to the patient from, for example, a non-HLA-matched donor.

Irrespective of the source of the cells (e.g., autologous or not), the decellularized solid organ can be autologous, allogeneic or xenogeneic to a patient.

In certain instances, a decellularized tissue may be recellularized with cells in vivo (e.g., after the tissue has been transplanted into an individual). In vivo recellularization may be performed as described above (e.g., injection and/or perfusion) with, for example, any of the cells described herein. Alternatively or additionally, in vivo seeding of a decellularized organ or tissue with endogenous cells may occur naturally or be mediated by factors delivered to the recellularized tissue.

Treatment

The present invention provides compositions and methods for treating various lung diseases and conditions using the cells of the invention. In some instances, the cells included genetically modified cells.

The present invention also may include treating one or more lung diseases or conditions by administering a cell of the present invention. In preferred embodiments of the invention, the compositions may be administered intratracheally. In the most preferred embodiments of the invention, intratracheal administration involves contacting or exposing lung tissue, e.g., pulmonary alveoli, to a cell of the present invention.

The compositions and methods of the present invention may be used to treat or inhibit any lung disease or condition in which it may be desirable to contact one or more lung tissues with a composition comprising cells of the invention. As used herein, diseases or conditions refers to any disease or condition that results in the pathological alteration of lung function or architecture. Exemplary diseases or conditions include, but are not limited to bronchopulmonary dysplasia (BPD), acute respiratory distress syndrome (ARDS), emphysema, cystic fibrosis (CF), pulmonary hypoplasia, and pulmonary hypertension, and chronic obstructive lung disease (COPD).

The compositions and methods of the present invention may be used to treat alveolar damage caused by any disease or condition. Exemplary diseases or conditions include, but are not limited to bronchopulmonary dysplasia (BPD), acute respiratory distress syndrome (ARDS), emphysema, and chronic obstructive lung disease (COPD).

The compositions and methods of the present invention may be used to treat or prevent any oxygen induced lung injury, disease, or condition. Exemplary diseases or conditions include, but are not limited to bronchopulmonary dysplasia (BPD), acute respiratory distress syndrome (ARDS), emphysema, cystic fibrosis (CF), pulmonary hypoplasia, pulmonary hypertension, and chronic obstructive lung disease (COPD).

In the context of gene therapy, the cells can be treated with a gene of interest prior to delivery of the cells into the recipient. In some cases, such cell-based gene delivery can present significant advantages of other means of gene delivery to the lung, such as inhalation of adenoviral gene delivery vectors. This superiority of cell-based gene delivery to a host stems from the observation that inhaled gene delivery vectors typically result in poor efficiency of cellular transduction, due to barriers imposed by the mucous layer and the host immune system. Delivery of a therapeutic gene that has been pre-inserted into cells avoids the problems associated with penetration of gene therapy vectors into recipient lung cells.

Accordingly, the invention provides the use of genetically modified cells that have been cultured according to the methods of the invention. Genetic modification may, for instance, result in the expression of exogenous genes ("transgenes") or in a change of expression of an endogenous gene. Such genetic modification may have therapeutic benefit. Alternatively, the genetic modification may provide a means to track or identify the cells so-modified, for instance, after implantation of a composition of the invention into an individual. Tracking a cell may include tracking migration, assimilation and survival of a transplanted genetically-modified cell. Genetic modification may also include at least a second gene. A second gene may encode, for instance, a selectable antibiotic-resistance gene or another selectable marker.

Proteins useful for tracking a cell include, but are not limited to, green fluorescent protein (GFP), any of the other fluorescent proteins (e.g., enhanced green, cyan, yellow, blue and red fluorescent proteins; Clontech, Palo Alto, CA), or other tag proteins (e.g., LacZ, FLAG-tag, Myc, His6, and the like).

When the purpose of genetic modification of the cell is for the production of a biologically active substance, the substance will generally be one that is useful for the treatment of a given disorder. For example, it may be desired to genetically modify cells so that they secrete a certain growth factor product associated with bone or soft tissue formation. Growth factor products to induce growth of other, endogenous cell types relevant to tissue repair are also useful. For instance, growth factors to stimulate endogenous capillary and/or microvascular endothelial cells can be useful in repair of soft tissue defect, especially for larger volume defects.

The cells of the present invention can be genetically modified by having exogenous genetic material introduced into the cells, to produce a molecule such as a trophic factor, a growth factor, a cytokine, and the like, which is beneficial to culturing the cells. In addition, by having the cells genetically modified to produce such a molecule, the cell can provide an additional therapeutic effect to the mammal when transplanted into a mammal in need thereof. For example, the genetically modified cell can secrete a molecule that is beneficial to cells neighboring the transplant site in the mammal.

The pulmonary cells may be genetically modified using any method known to the skilled artisan. See, for instance, Sambrook et al. (2012, Molecular Cloning: A Laboratory Manual, Cold Spring Harbor Laboratory Press, Cold Spring Harbor, New York), and in Ausubel et al, Eds, (1997, Current Protocols in Molecular Biology, John Wiley & Sons, New York, NY). For example, a pulmonary cell may be exposed to an expression vector comprising a nucleic acid including a transgene, such that the nucleic acid is introduced into the cell under conditions appropriate for the transgene to be expressed within the cell. The transgene generally is an expression cassette, including a polynucleotide operably linked to a suitable promoter. The polynucleotide can encode a protein, or it can encode biologically active RNA (e.g., antisense RNA or a ribozyme). Thus, for example, the polynucleotide can encode a gene conferring resistance to a toxin, a hormone (such as peptide growth hormones, hormone releasing factors, sex hormones, adrenocorticotrophic hormones, cytokines (e.g., interferins, interleukins, lymphokines), etc.), a cell-surface-bound intracellular signaling moiety (e.g., cell adhesion molecules, hormone receptors, etc.), a factor promoting a given lineage of differentiation (e.g., bone morphogenic protein (BMP)), etc.

Within the expression cassette, the coding polynucleotide is operably linked to a suitable promoter. Examples of suitable promoters include prokaryotic promoters and viral promoters (e.g., retroviral ITRs, LTRs, immediate early viral promoters (IEp), such as herpesvirus IEp (e.g., ICP4-IEp and ICPO-IEEp), cytomegalovirus (CMV) IEp, and other viral promoters, such as Rous Sarcoma Virus (RSV) promoters, and Murine Leukemia Virus (MLV) promoters). Other suitable promoters are eukaryotic promoters, such as enhancers (e.g., the rabbit .beta.-globin regulatory elements), constitutively active promoters (e.g., the .beta.-actin promoter, etc.), signal specific promoters (e.g., inducible promoters such as a promoter responsive to RU486, etc.), and tissue-specific promoters. It is well within the skill of the art to select a promoter suitable for driving gene expression in a predefined cellular context. The expression cassette can include more than one coding polynucleotide, and it can include other elements (e.g., polyadenylation sequences, sequences encoding a membrane-insertion signal or a secretion leader, ribosome entry sequences, transcriptional regulatory elements (e.g., enhancers, silencers, etc.), and the like), as desired.

The expression cassette containing the transgene should be incorporated into a genetic vector suitable for delivering the transgene to the cells. Depending on the desired end application, any such vector can be so employed to genetically modify the cells (e.g., plasmids, naked DNA, viruses such as adenovirus, adeno-associated virus, herpesviruses, lentiviruses, papillomaviruses, retroviruses, etc.). Any method of constructing the desired expression cassette within such vectors can be employed, many of which are well known in the art (e.g., direct cloning, homologous recombination, etc.). The choice of vector will largely determine the method used to introduce the vector into the cells (e.g., by protoplast fusion, calcium-phosphate precipitation, gene gun, electroporation, DEAE dextran or lipid carrier mediated transfection, infection with viral vectors, etc.), which are generally known in the art.

Examples of techniques sufficient to direct persons of skill through in vitro amplification methods, including the polymerase chain reaction (PCR), the ligase chain reaction (LCR), and other DNA or RNA polymerase-mediated techniques are found in Sambrook et al. (2012, Molecular Cloning: A Laboratory Manual, Cold Spring Harbor Laboratory Press, Cold Spring Harbor, New York).

Once the nucleic acid for a protein is cloned, a skilled artisan may express the recombinant gene(s) in a variety of lung cells. It is expected that those of skill in the art are knowledgeable in the numerous expression systems available for expressing the desired transgene.

Lung Cells

Differentiation can be induced using one or more differentiation agents, including without limitation, $Ca^{2+}$, an epidermal growth factor (EGF), a platelet derived growth factor (PDGF), a keratinocyte growth factor (KGF), a transforming growth factor (TGF), cytokines such as an interleukin, an interferon, or tumor necrosis factor, retinoic acid, transferrin, hormones (e.g., androgen, estrogen, insulin, prolactin, triiodothyronine, hydrocortisone, or dexamethasone), sodium butyrate, TPA, DMSO, NMF (N-methyl formamide), DMF (dimethylformamide), or matrix elements such as collagen, laminin, heparan sulfate).

In one embodiment, MSCs can be induced to differentiate into cells having a lung phenotype. For example, the MSCs can be induced to differentiate into type II alveolar cells, which also are known as type II pneumocytes. In another embodiment, the MSCs can be induced to differentiate into Clara cells.

A medium can be used that contains one or more of pituitary extract (e.g. a bovine pituitary extract), steroid hormones (e.g. hydrocortisone, or a salt thereof such as the acetate), growth factors (e.g., epidermal growth factor, preferably human epidermal growth factor), catecholamines (e.g., epinephrine, either in racemic or enantiomeric form), iron-binding proteins (e.g., a transferrin), insulin, vitamins (e.g., retinoic acid), thyroid hormones (e.g., triiodothyronine), serum albumins (e.g., bovine or human serum albumin, including recombinant preparations), antibiotics (e.g., aminoglycoside antibiotics, such as gentamicin), and/or antifungals (e.g., amphotericin-B). For example, a medium can include hydrocortisone, epidermal growth factor, insulin, triiodothyronine, transferrin, and bovine serum albumin and in some embodiments, further can include retinoic acid, pituitary extract, and epinephrine. SAGM™ medium from Cambrex (catalog CC-3118) is particularly useful for differentiating MSCs into a desired lung cell.

The present inventors have been able to obtain, through use of appropriate differentiation factors and culturing conditions, a pure population of lung cells. In one embodiment, the lung cell is a distal lung cell type, preferably an alveolar-type cell, more preferably, a type-I or type-II alveolar-type cell. In another embodiment, the lung cell is a Clara cell.

In some embodiments, the methods of the invention efficiently induce direct differentiation of MSCs into alveolar type II cells. In some embodiments, the method results in a sufficiently pure population of alveolar type II cells (e.g., at least 95% alveolar type II phenotype).

In some embodiments, the methods of the invention efficiently induce direct differentiation of MSCs into Clara cells. In some embodiments, the method results in a sufficiently pure population of Clara cells (e.g., at least 95% Clara cell phenotype).

Differentiation to lung cells (e.g., alveolar type II cells) can be confirmed, for example, by a lung morphology as assessed by light microscopy and the presence of lamellar bodies and microvesicular bodies as assessed by transmission electron microscopy. Lamellar bodies are secretory lysosomes that serve as the storage form of lung surfactant, surfactant protein C (SPC), which is an integral membrane protein that is expressed only in alveolar type II cells. The presence of SPC mRNA can be detected by reverse-transcriptase PCR and the presence of SPC protein can be detected by immunofluorescence staining. Clara cell differentiation can be assessed by detecting the presence of CCSP.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Epithelial Cell Differentiation of Human Mesenchymal Stromal Cells Varies Depending on Tissue of Origin when Cultured in Decellularized Lung Scaffolds In experiments presented herein, the potential of human derived BM-MSCs as well as AT-MSCs to contribute to lung epithelium following culture on rat decellularized lung matrices was evaluated. It was found that hBM-MSCs and hAT-MSCs are capable of attachment and growth following seeding onto the lung scaffold. Following seven days of culture in decellularized rat lung scaffolds in small airway growth medium (SAGM), the hBM-MSCs express the type 2 pneumocyte marker, pro-SPC at the RNA and protein level, secrete surfactant into the culture medium and contain lamellar bodies as shown by transmission electron microscopy (TEM). Additionally, hBM-MSC cells give rise to cells that are positive for the proximal airway marker, cytokeratin-5, after culture in the rat bioreactor. In contrast, the hAT-MSCs give rise to pro-SPC positive cells as well as Clara-like cells that line the airways in anatomically correct positions. However, the hAT-MSCs do not give rise to cytokeratin-5 positive cells following culture in the lung bioreactor unlike hBM-MSCs.

The influence of substrate matrix composition in the differentiation of the mesenchymal stromal cells was also explored by seeding hBM-MSCs and hAT-MSCs onto tissue culture dishes coated with Human ECM, Matrigel, laminin, collagen 1, collagen 4, and fibronectin. It is demonstrated herein that matrix surface coatings influence the percentage of MSCs that express lung epithelial markers when grown in standard tissue culture flasks. Additionally hBM-MSCs were cultured on decellularized liver and show that MSCs seeded onto liver slices do not maintain the same suite of epithelial markers present when these are cultured on the lung matrix These data indicate that the decellularized lung scaffolds retain "zip-codes" to direct cell differentiation. The present data demonstrates that human derived hBM-MSCs and hAT-MSCs can give rise to multiple lung epithelial cell types when placed onto a decellularized lung.

The materials and methods employed in these studies are now described.

Isolation and Characterization of Human Bone Marrow and Adipose Tissue Mesenchymal Stromal Cells Fresh, unprocessed human bone marrow samples were acquired from Lonza, Allendale, NJ, USA (cat #1M-125). Three total donor samples were acquired, two female and one male ages ranging between 22-29. The bone marrow cells were plated at a density of $5 \times 10^5$ cells per cm$^2$ in high glucose DMEM containing 10% FBS. The media was changed every two to three days. Only low passage ($\leq 5$) cells were used in experiments. Cells were passaged every 7-10 days at a 1:3 ratio. Cells were characterized by flow cytometry (BD LSR II) for expression of CD90, CD105, CD73, CD45 (all antibodies were acquired from eBiosciences).

AT-MSCs were acquired from three donors ranging in age from 44-63. Lipoaspirates were washed 2× with DPBS, followed by digestion with 0.15% collagenase Type 1 (Gibco, Grand Island, NY, USA, CAT #17100-017) in DMEM for 60 minutes at 37° C. The digest was stopped by adding 10% FBS/DMEM, followed by centrifugation and resuspension in 10% FBS/DMEM and filtration through a 100 μm filter. Cells were fed every 2-3 days.

FACS

Single cells were fixed with a 2% paraformaldehyde solution for 10 minutes, and washed 2 times in PBS for 5 minutes each. The cells were incubated with 10% FBS, 0.2% Triton X-100 containing the diluted antibody of interest. The cells were incubated on ice with the following antibodies (all from eBiosciences, San Diego, CA, USA) for 25 minutes in the dark: CD45-PE (12-9459-41), CD90-FITC (11-0909-41), CD73-PE (12-0739-41), CD105-APC (17-1057-41). Additional antibodies used were: pro-SPC 1/100 (Millipore, Billerica, MA, USA: ab 3786), and CCSP 1/100 (Millipore 07-623). Secondaries for these antibodies were all species appropriate Invitrogen Alexa Fluors diluted at 1/500. Isotype controls used included, anti-mouse IgG-PE (eBiosciences 12-4714), anti-mouse IgG-FITC (ebiosciences11-4724), anti-mouse IgG APC (ebiosciences 17-4015-80), rabbit IgG-FITC (ebiosciences 11-4614-80), and purified rabbit IgG (Invitrogen 02-6102). In addition to isotype controls, secondary only antibody controls were run in parallel.

Decellularization and Reseeding of Rat Lung Samples

Adult Sprague Dawley rat lungs (between 3 and 5 months old) were decellularized as previously described (Petersen et al., 2010, Science 329:538-541). Briefly, rats were euthanized with an IP injection of sodium pentobarbital (Euthasol). The rat lungs were excised and the trachea and pulmonary artery were cannulated. A 10 ml mixture of heparin (50 U/ml) and sodium nitroprusside (1 μg/ml) was infused by gravity through the pulmonary artery. The pulmonary artery was instilled with 500 ml of pH 12 decellularization solution composed of 8 mM CHAPS, 25 mM EDTA, 1 M NaCl in PBS at 37° C. at a constant pressure of 20 mmHg. The lungs were then infused via the airways with 10 ml of benzonase and incubated for 1 hr at 37° C. The cellular remnants were washed away with 2.5 L of PBS. The lungs were incubated in a mixture of antibiotics and antimycotics (1% gentamicin, 4 mg/ml amphotericin, 10% penicillin/streptomycin) for at least 16 hours prior to seeding with cells. During this incubation the solution was perfused through the pulmonary artery at 1 mL/min. Prior to seeding cells, the antibiotic/antimycotic solution was removed from the lungs and replaced with PBS. The lungs were perfused with PBS for an additional 30 minutes before cellular seeding. Cells were seeded as a bolus of between $2.5 \times 10^6$ to $10 \times 10^6$ cells through the trachea into the single decellularized upper right rat lung lobe. The cultures were maintained for 7 days in SAGM (Lonza, Allendale, NJ; CAT #CC-3118) with perfusion of the media via the pulmonary artery at 1 ml/min. Media was changed every 2-3 days.

Immunohistochemistry

Lungs were instilled with a 10% formalin solution through the airways, and placed in 10% formalin for 4 hours at room temperature with constant rocking. Lungs were embedded in paraffin, and sectioned at 5 microns. The sections were deparaffinized following a standard rehydration alcohol/xylene series. Antigen retrieval was performed by incubation of the rehydrated tissue sections with a Tris-EDTA buffer (10 mM Tris Base, 1 mM EDTA, 0.05% Tween-20 at pH 9.0) at 75° C. for 20 minutes. The tissue sections were then allowed to cool at room temperature for an additional 20 minutes. The sections were washed once in PBS prior to immunostaining. The sections were incubated in blocking reagent (10% NGS or FBS, 0.2% Triton X-100 in PBS) for 45 minutes. The primary antibodies (CCSP 1/50: Millipore Cat. #07-623; pro-SPC 1/100: Millipore: #ab 3786; caveolin-1 1/100: Abcam, Cambridge, UK #39541; alpha smooth muscle actin 1/100: Dako, Glostrup, Denmark Cat. #M0851) were incubated for 2 hours at room temperature, or overnight at 4° C. The sections were washed in PBS 3 times for 3 minutes per wash, followed by incubation with secondary antibodies (all species specific secondary antibodies from Invitrogen Alexa Fluor series diluted at 1/500) at room temperature for 45 minutes. Tissue sections were mounted in Vector labs Vectashield mounting medium containing DAPI (Vector cat., Olean, NY #H1200).

Processed sections were imaged with a Zeiss fluorescence microscope and images acquired with Volocity software. Confocal microscope images were acquired with a Leica TCS SP5.

Real Time Quantitative RT-PCR

Total RNA was extracted from cells using the RNeasy Mini Kit from Qiagen following the manufacturer's instructions. First-strand complementary DNA (cDNA) was synthesized with random hexamers as primers, using the SuperScript First-Strand Synthesis System according to manufacturer's protocol (Invitrogen). An equal volume mixture of the products was used as templates for PCR amplification. Reactions were performed in a 25 μl volume with iQ SYBR Green Supermix (Bio-Rad, Hercules, NY) and 200 nM each of forward and reverse primers shown using iCyler and iQ software (Bio-Rad). Each sample was run in triplicate. PCR conditions included an initial denaturation step of 4 min at 95° C., followed by 40 cycles of PCR consisting of 15 s at 95° C., 30 s at 60° C., and 30 s at 72° C. Average threshold cycle (Ct) values from the triplicate PCR reactions for a gene of interest (GOI) were normalized against the average Ct values for GAPDH from the same cDNA sample. Fold change of GOI transcript levels between sample A and sample B equals $2^{-\Delta\Delta Ct}$, where $\Delta Ct = Ct_{(GOI)} - Ct_{(GAPDH)}$, and $\Delta\Delta Ct = \Delta Ct_{(A)} - \Delta Ct_{(B)}$. Primers used are listed elsewhere herein.

Statistical Analyses

All statistical analyses were performed with the Origin software (OriginLab, Northampton, MA). The data were expressed as mean±s.e.m. (standard error of measurement). T-tests were performed to evaluate whether two groups were significantly different from each other and $p \leq 0.05$ was considered statistically significant.

TEM

A modified protocol from Schmiedl et al. 2005 was followed (Schmiedl, et al., 2005, Histochem Cell Biol 124(6):465-76). Native rat lungs and recellularized lungs were inflation fixed at 37° C. with 2.5% glutaraldehyde/2.0% paraformaldehyde in 0.2M sodium cacodylate for 30 minutes, followed by a 2-hour incubation at 4° C. The fixed tissue was rinsed with 0.1M sodium cacodylate. The tissues were post-fixed in 1% $OsO_4$ for 2 hours, followed by en block uranyl acetate staining. The tissues were dehydrated in a standard ethanol series and embedded in EPON. Sections (70 nm) were obtained and post-stained with uranyl acetate and lead citrate. Images were obtained with a Philips Tecnai transmission electron microscope.

Coating of Matrix Proteins for Cell Culture hBM-MSC and hAT-MSC was cultured on different extracellular proteins including fibronectin (50 μg/ml), collagen I (100 μg/ml), collagen IV (50 μg/ml), Matrigel (1:80), and a mixture of human ECM proteins (1:100) (consisting of collagens, laminin, fibronectin, tenascin, elastin, and a number of proteoglycans and glycosaminoglycans; Sigma) for 7 days. Fibronectin, collagen I, collagen IV and laminin are principal components of lung matrix.

Enzyme-Linked Immunosorbent Assay Analysis (ELISA) for SPC

ELISA was performed on cell culture media collected from the supernatant of hBM-MSCs and hAT-MSCs cultured on rat acellular lung scaffolds to quantify secreted SPC according to the manufacturer's instructions (Life Science Advanced Technology). SPC values were normalized to the total number of cells, and values for experimental samples were subtracted from fresh SAGM medium alone.

The results of the experiments are now described.

Figure 1F:
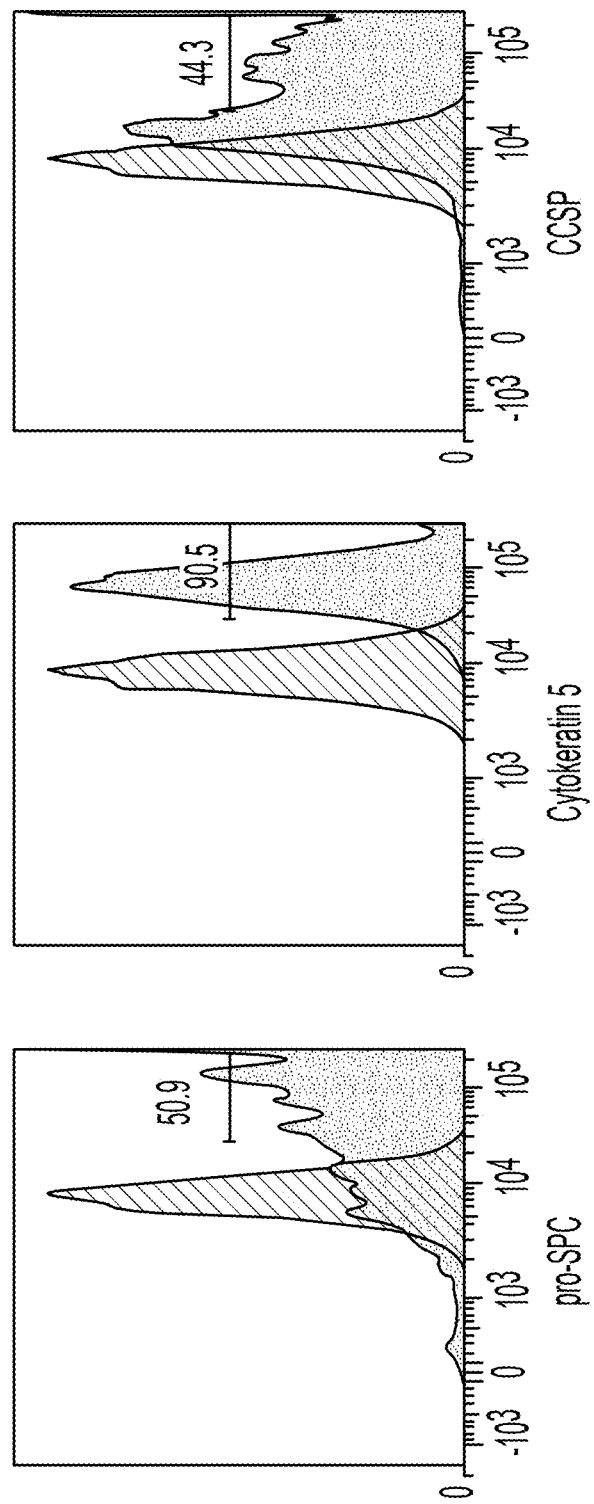
Figure 12:
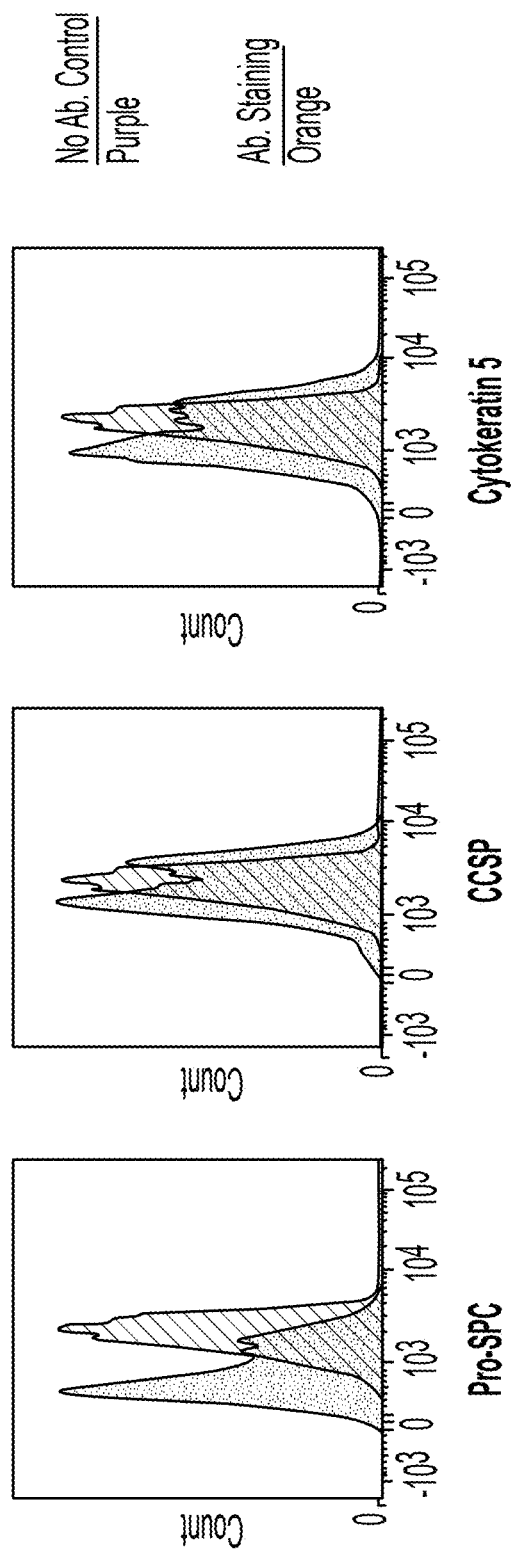
FIG. 12 is a panel of graphs showing whole, unfractionated human bone marrow cells as negative staining control for lung epithelial markers. Unfractionated human bone marrow mononuclear cells were stained for lung epithelial markers, pro-SPC, CCSP, and cytokeratin-5. There was no indication of unfractionated cells having positive marker expression. The right shaded peaks indicate no antibody control; the left peaks indicate cells incubated with antibodies.

Characterization of MSCs Isolated from Bone Marrow and Adipose Tissue hBM-MSCs were obtained from freshly isolated bone marrow samples (FIG. 1A-1C). The unfractionated marrow was placed on tissue culture flasks and the resultant adherent cells were immunophenotyped for expression of canonical MSC cluster of differentiation markers. Early passage hBM-MSCs, between 2 to 4 passages, were greater than 93% positive for CD90, CD105, and CD73, while being predominantly negative for CD45 (FIG. 1B). Cells were also assayed for the expression of epithelial markers including CCSP, pro-SPC and cytokeratin 5 (FIG. 1C), since previous work has shown a sub-fraction of cultured MSC-like cells can express epithelial markers (Wong, et al., 2009, J Clin Invest 119(2):336-48). FACS analysis revealed that hBM-MSCs express epithelial markers following standard culture in 10% FBS/DMEM. The data presented herein indicate that hBM-MSCs are positive for CCSP (80%), pro-SPC (63%), and cytokeratin-5 (77%) by FACS analysis (FIG. 1C). As a negative control for these experiments, whole unfractionated bone marrow mononuclear cells were analyzed by FACS and these were uniformly negative for the lung epithelial markers assess (FIG. 12). hAT-MSC were isolated from freshly harvested lipo-aspirates (FIG. 1D-1F).

The cells were isolated via collagenase 1 tissue digest and placed onto tissue culture flasks. These cells were maintained in 10% FBS/DMEM medium for expansion. Immunophenotyping of hAT-MSCs confirmed their identity as CD90+/CD105+/CD73+ and CD45− (FIG. 1E). Similar to hBM-MSCs, hAT-MSCs were immunopositive by FACS for various epithelial markers (FIG. 1F). Interestingly, there were differences in the total amount of cells that express epithelial markers between the hAT-MSCs and the hBM-MSCs. In contrast to the hBM-MSC population, approximately half of the population of hAT-MSCs is positive for CCSP (44%); hAT-MSCs are also positive for pro-SPC (51%), and cytokeratin 5 (91%) (FIG. 1F).

Repopulation of Rat Acellular Matrix with MSCs in Lung Bioreactors hBM-MSCs Reseeded Onto Rat Lung Acellular Matrix In an effort to understand whether adipose or bone marrow derived MSCs are capable of recellularizing the rat acellular matrix, and whether these cells are able to take on an epithelial phenotype after placement on the acellular matrix, MSCs were cultured in a previously described biomimetic rat lung bioreactor system (Petersen et al., 2010, Science 329:538-541). Prior to seeding MSCs into the decellularized lung scaffolds, H&E histology and DAPI staining of the native and the decellularized lung matrix were observed. These analyses confirm that the decellularized lung is devoid of remnant native lung cells (FIG. 2A-B).

hBM-MSCs cultured from between 2 to 4 passages were seeded via the airway at a density between 2.5-10 million cells into the single right upper lobe of a decellularized rat lung. These cells were injected as a bolus into the trachea and cultured in the lung bioreactor for 7 days in small airway growth medium (SAGM). SAGM was chosen as a potentially suitable medium for the culture of the recellularized lung after pilot experiments with 10% FBS/DMEM resulted in cells that were uniformly fibroblastic in morphology, with nearly all cells expressing α-sma, a marker of myofibroblasts, following a week of culture (FIG. 7). SAGM was selected as a good candidate to promote lung epithelial differentiation because of the retinoic acid and human epidermal growth factor it contains has been shown to promote proliferation and epithelial differentiation of pluripotent cells (Rackley & Stripp, 2012, J Clin Invest 122:2724-2730; Lenssen & Stolk, 2007 Int J Chron Obstruct Pulmon Dis. 2(2):131-139). In vitro pilot experiments were performed in which MSCs were grown in tissue culture flasks with SAGM medium or in 10% FBS/DMEM. These experiments demonstrated that MSCs grown in SAGM were devoid of cells positive for α-sma, while the cells maintained CCSP expression to a similar level (FIG. 7C-7F).

As a result of the in vitro experiments, SAGM was used in an effort to curb the amount of cells that express a-sma and in turn promote lung epithelial differentiation. However, prior to seeding the hBM-MSCs into the acellular lung, the cells were maintained in 10% FBS/DMEM medium to promote robust growth.

H&E staining of hBM-MSC reseeded lungs cultured for 7 days in SAGM demonstrated a more cuboidal appearance of the attached cells, when compared to cells that were grown in 10% FBS/DMEM in the lung bioreactor (FIG. 2C and FIG. 7). In agreement with the in vitro cultures, immunostaining for a-sma was almost entirely absent in the hBM-MSC recellularized rodent lungs. Additional staining for lung epithelial markers established that between 65-70% of the attached cells expressed pro-SPC, a type 2 pneumocyte marker (FIG. 2D). Cytokeratin-5, a marker expressed by basal epithelial cells of the airways, was also present in a subset of the attached cells (FIG. 2F). Interestingly, there were no cells that were positive for CCSP after culture in the lung bioreactor, even though the starting population of hBM-MSCs expressed CCSP by immunostaining and FACS (FIG. 2E; FIG. 1C). The attached cells were also negative for P63, a marker of basal cells, and caveolin-1, a marker of type 1 pneumocytes.

In order to gain insight into the possible function and full differentiation state of the pro-SPC positive cells that are derived from hBM-MSCs, it was sought to identify type 2 pneumocyte lamellar bodies, as well as the surfactant vesicles secreted by these cells, with transmission electron microscopy (FIG. 2H). The identification of lamellar bodies via transmission electron microscopy of native lung type 2 pneumocytes is an often times used method of positive identification of type 2 cells (Schmiedl, et al., 2005, Histochem Cell Biol 124(6):465-76). The presence of lamellar bodies can also be an indication of function within these cells (Kassmer & Krause, 2010, Experimental Hematology 38:564-573). Lamellar bodies serve as a repository of secretory surfactants and lipids contained within the type 2 cells. Both human and rat type 2 pneumocytes are characterized by the presence of lamellar bodies. As a positive control, the presence of lamellar bodies within type 2 pneumocytes of the native rat lung was investigated (FIG. 2B, blue arrows). These lamellar bodies are approximately 500 nm long and are characterized by electron-dense deposits in structures that are formed of concentric whorls. Additionally, another characteristic of native type 2 pneumocytes is the presence of secretory vesicles (FIG. 2G, white arrows).

Lung decellularized scaffolds that were seeded with hBM-MSCs only—no other cell types—and cultured for 7 days, were also assayed for the presence of lamellar bodies as well as secretory vessels in adhered cells (FIG. 2H). These hBM-MSC-derived cells had abundant electron dense lamellar bodies, as well as many secretory vesicles (arrows and chevrons, respectively FIG. 2H). Morphologically, the native rat type 2 pneumocytes were very similar to the hBM-MSCs that had been cultured within the bioreactor on lung matrix and in the presence of SAGM for 7 days. Collectively, these data indicate that the hBM-MSCs not only express the markers associated with type 2 pneumocytes at the protein level, but also have cytoplasmic structures associated with function that is similar to that contained within native type 2 cells. Hence, the present data demonstrates that hBM-MSC can take on the phenotype of type II alveolar epithelial cells, when expanded and cultured under suitable conditions.

hAT-MSCs Reseeded Onto Rat Lung Acellular Matrix

To determine the capacity of hAT-MSCs to engraft onto the decellularized lung, $2.5\text{-}10\times10^6$ cells were seeded as a bolus into the upper right decellularized rodent lung lobe and were cultured in SAGM medium for 7 days under the same conditions as the hBM-MSCs. H&E histological preparations of seeded lungs demonstrated that the hAT-MSCs were able to attached throughout the matrix, but had a particular affinity to attach and repopulate the airways, unlike the hBM-MSCs which do not attach in the airways (FIG. 3A-B). Immunostaining revealed that the cells attached to the airways were positive for CCSP, a marker of Clara cells. This is in contrast to hBM-MSCs, which do not maintain expression of CCSP following culture on the lung matrix, nor do these cells adhere to the airways.

hAT-MSCs cultured in the lung bioreactor also were positive for the type 2 pneumocyte marker, pro-SPC. Immunofluorescence for pro-SPC revealed cells with clear, punctate cytoplasmic staining for this marker (inset FIG. 3C). Another difference between hAT-MSCs and hBM-MSCs following culture is that the hAT-MSCs do not give rise to cells that are cytokeratin-5 positive by immunofluorescence, whereas the hBM-MSCs do (FIGS. 3D and 2H). These data indicate that there are intrinsic differences between MSCs derived from different tissue sources with regard to their ability to repopulate the lung acellular matrix.

Alveolar Epithelial Gene Expression Following Lung Bioreactor Culture

Gene expression for various distal lung epithelial markers were also evaluated in the hBM-MSC and hAT-MSC recellularized lungs. Real-time qRT-PCR was used to assay for expression of surfactant protein C (type II), caveolin-1 and aquaporin 5 (AQP5, type I) (FIG. 4).

Surfactant protein C (SPC) is widely used as a marker of Type II pneumocytes as well as early lung progenitor cells. RT-PCR revealed that SPC expression in hBM-MSC recellularized lungs increased when comparing bioreactor cultures at day 3 and day 7, to MSCs grown in a flask (FIG. 4A). These results show that there is a progressive increase in the amounts of SPC transcripts present at day 3 and day 7 by 23 and 93 fold, respectively (FIG. 4A).

A similar pattern of SPC expression was observed in the hAT-MSC seeded lung scaffolds. The expression of SPC increased from day 3 (36×) to day 7 (137×) when compared to hAT-MSC grown in flasks. The increase in SPC gene expression was greater for the hAT-MSC recellularized lungs when compared to the hBM-MSC recellularized lungs.

Additionally, the expression of two specific alveolar type I markers including caveolin-1 and AQP5 were evaluated in hBM-MSC and hAT-MSC seeded rat lung scaffolds. The gene expression of both caveolin-1 and AQP5 increased over time in the lung bioreactor culture as assessed on day 3 and day 7, when compared with MSCs grown on tissue culture flasks (FIG. 4B-F). While the gene expression for these two type 1 cell markers increased with time in culture protein expression based on immunostaining for the type one marker, caveolin-1 or aquaporin 5 was unable to be detected.

Overall, qRT-PCR revealed that the levels of gene expression for SPC, caveolin-1 and AQP5 increased with time in the bioreactor with both hBM-MSC and hAT-MSC seeded lung scaffolds. However, protein expression as shown by immunostaining indicates that of these genes only pro-SPC is detectable in hBM-MSCs and AT-MSC after 7 days on the lung scaffold, while there is no detectable expression for the type 1 markers. While not wishing to be bound by any particular theory, this apparent discrepancy is likely explained by protein levels that are not robust enough for detectable signal with immunostaining, whereas the sensitivity of qRT-PCR allows us the capacity to detect small amounts of mRNA expression from the cells seeded on the lung scaffold.

Functionality of Type 2 Pneumocytes Derived from hBM-MSCs and hAT-MSC

To determine if the MSCs seeded onto the decellularized lung scaffolds provided a functional improvement to the organ, it was assessed whether there was active surfactant secretion into the media by the cells growing on the decellularized scaffold (FIG. 5). hBM-MSCs were seeded at a density of 2×10$^6$ cells into the upper right decellularized lung lobe, and allowed to attach to the matrix for 2 hours, followed by cutting the lobe in half, and placing the pieces in a 6 well culture plate containing SAGM. The lung slices, thus seeded, were cultured for either 3 or 7 days and medium was collected at these time points. RT-PCR indicated an increase in SPC gene expression between days 3 and 7 when compared to the decellularized scaffold alone (FIG. 5A, 5B). Brightfield microscopy of active cultures revealed a visible layer of oil-like droplets that were mostly concentrated near the lung piece (FIG. 5D, 5E). As a control for these experiments, scaffolds that were not seeded with MSCs were placed in the same culture conditions. These controls did not contain oil-like droplets (FIG. 8). Because of the likelihood that the visible droplets were surfactant that was actively being produced by the seeded cells, ELISA was performed to test for the presence of surfactant protein C (FIG. 5C). Surfactant protein C was present in hBM-MSC slice cultures both at day 3 and day 7, at 3.3 ng/mL and 0.26/mL, respectively (FIG. 5C). The lung cultures seeded with hAT-MSC had a larger amount of surfactant protein present in the culture medium. The conditioned SAGM from these cultures contained 5.55 ng/mL and 1.16 ng/mL, respectively (FIG. 5C). These data indicate that the seeded MSCs take a function akin to type 2 pneumocytes in that the MSCs actively produce and secrete surfactant when cultured on decellularized lung scaffolds.

Influence of Substrate Matrix on the Differentiation of MSCs

In an effort to further understand the influence of the culture substrate on the differentiation of MSCs, either hAT-MSCs or hBM-MSCs were cultured on tissue culture flasks that had been coated with various extracellular matrix (ECM) proteins including collagen 1, collagen IV, laminin, fibronectin, human ECM, and Matrigel (FIG. 6). Collagen 1, collagen IV, laminin and fibronectin were chosen because each is a represented component of lung ECM (Petersen et al., 2012, Cells Tissues Organs 195:222-231; Cortiella et al., 2010, Tissue Eng Part A 16:2565-2580); the human ECM and Matrigel coatings were chosen in an effort to provide the cells with a mixed ECM composition. After a seven-day culture period in SAGM the population of cells was characterized for epithelial marker expression by FACS and by RT-PCR.

Figure 9A:
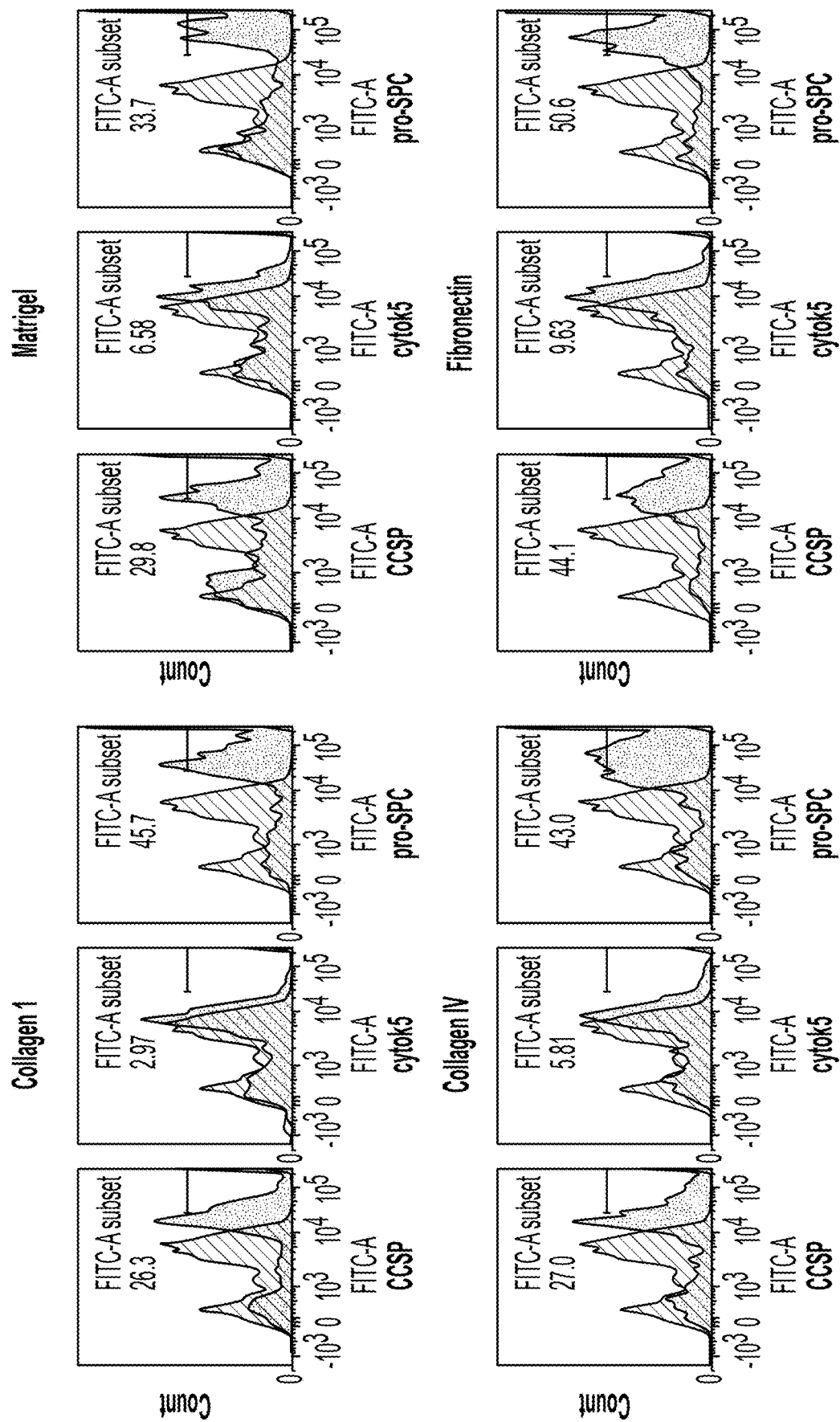
FIG. 9A-B is a set of FACS plots of hBM-MSCs grown on tissue culture flasks n SAGM for 7 days on different ECM substrates.
Figure 9B:
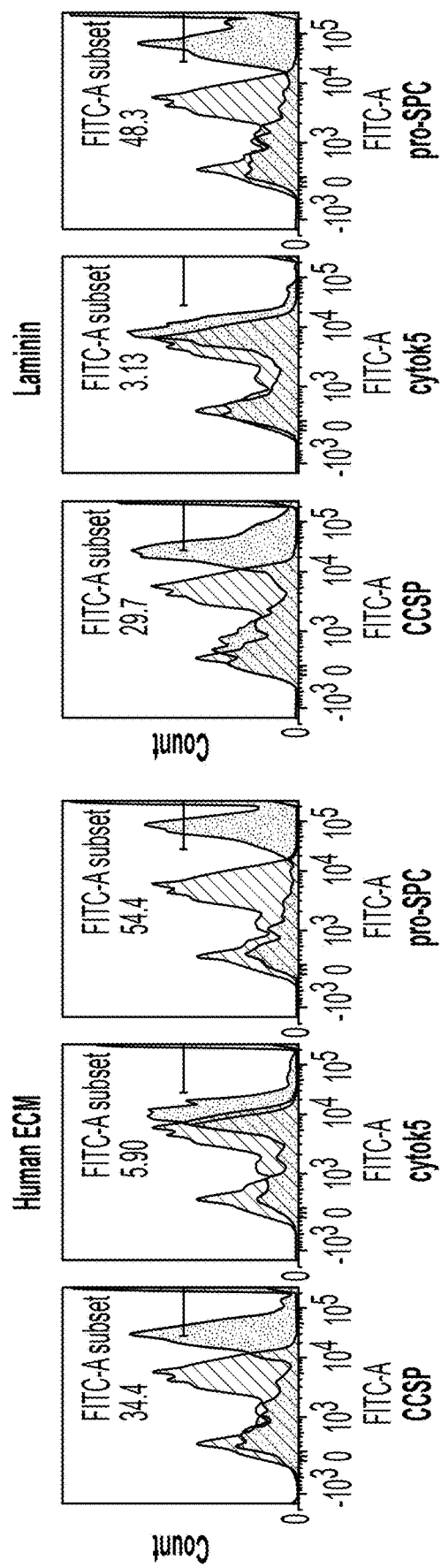
Figure 10A:
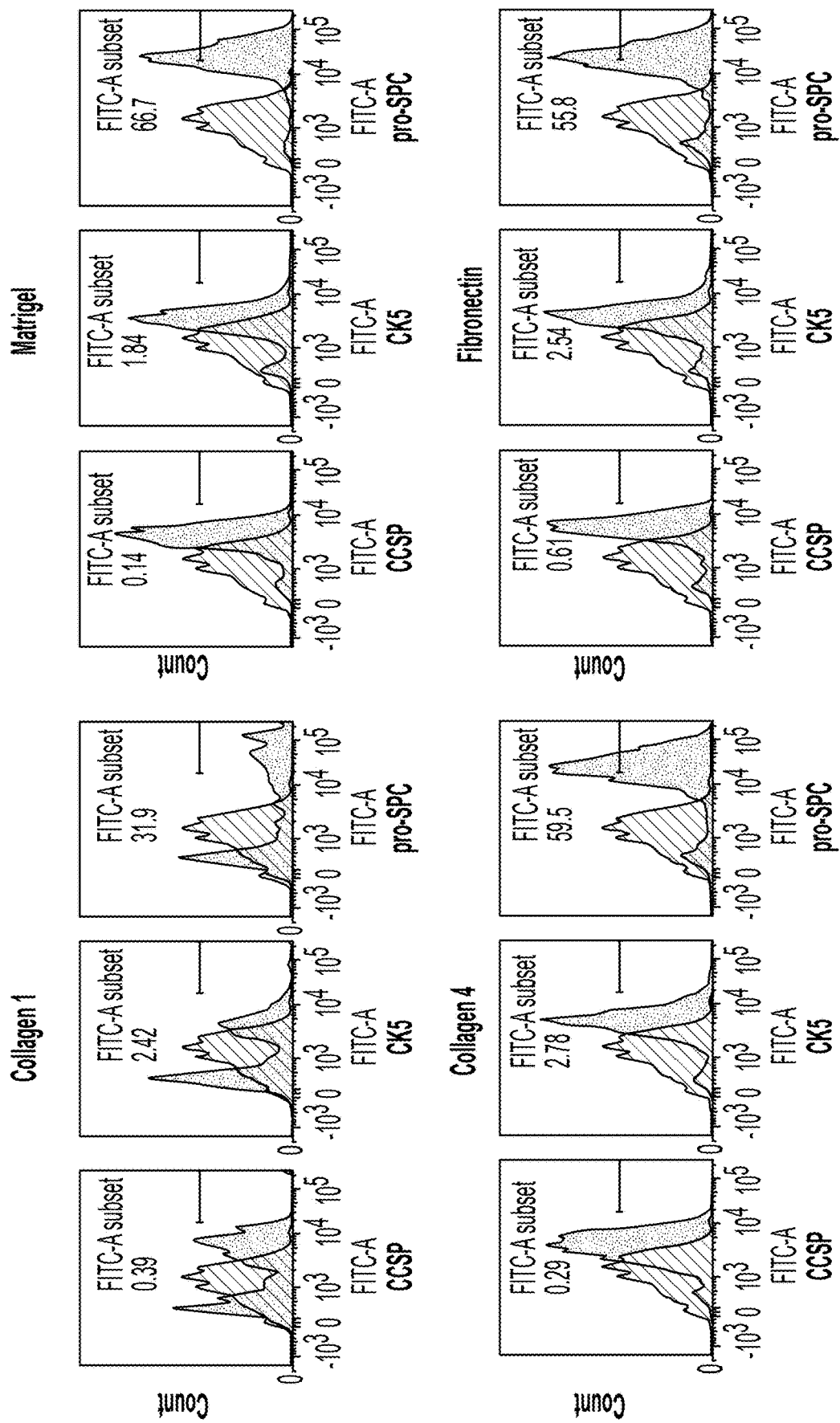
FIG. 10A-B is a set of FACS plots of hAT-MSCs grown on tissue culture flasks, in SAGM for 7 days on different ECM substrates.
Figure 10B:
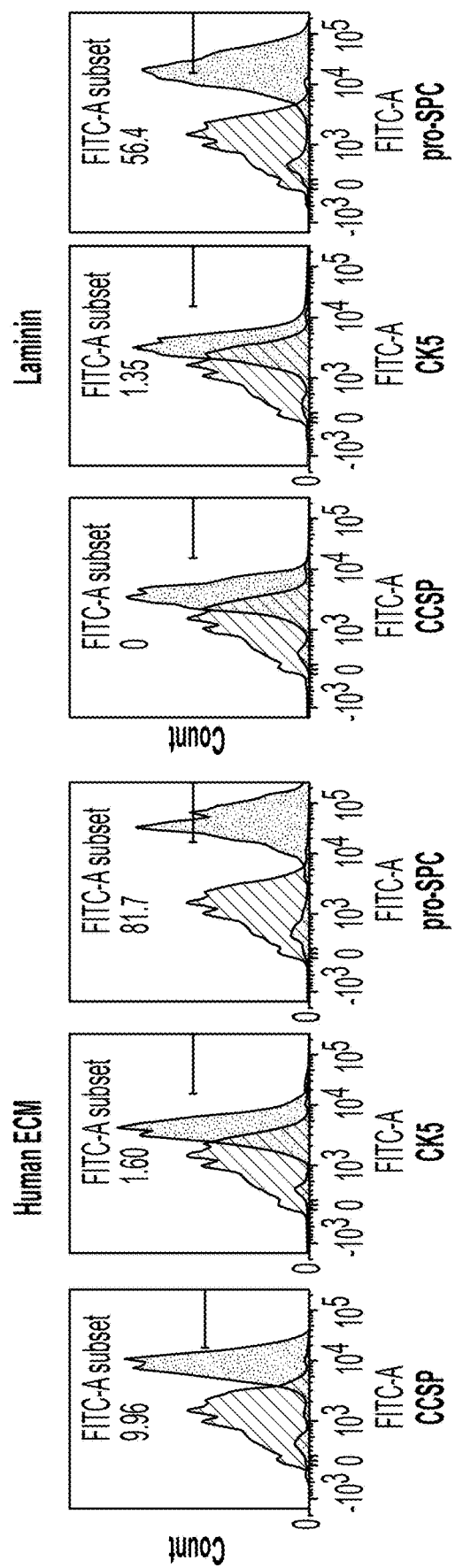

Data obtained from FACS analysis experiments from hBM-MSCs cultured on the variant substrates revealed large differences in the population of cells that expressed cytokeratin 5, CCSP and pro-SPC depending on the ECM component on which the cells were cultured (FIG. 6A, FIG. 9, and FIG. 10). Cells grown on collagen 1 substrate had the lowest amount of cells that were cytokeratin 5 positive; approximately 3.0% of the population was positive, a reduction of approximately 3 fold when compared to cells that were grown on fibronectin coated plastic flasks. The amount of CCSP positive cells in the hBM-MSC populations also varied drastically depending on the substrate on which these were grown. The largest population of CCSP positive cells was in the fibronectin coated flasks (44%), whereas the least amount of CCSP positive cells was found in hBM-MSCs grown on collagen 4 (27%). Likewise, the population of hBM-MSCs that express pro-SPC varied between surface coatings where the highest amount of cells positive was present in the human ECM coated flasks (54%), while the lowest was in cells grown on Matrigel (34%).

The behavior of hAT-MSCs grown on different ECM matrices also showed differences in the populations that express CCSP, pro-SPC and cytokeratin-5. For example, the population of pro-SPC positive cells ranged from a high of 81% in the human ECM condition to a low of 32% in the collagen 1 condition. The population of CCSP positive cells also was greatest in the human ECM coated flasks (10%), when compared to the other surface coatings. While there existed differences in the amount of cells that expressed epithelial markers between the hAT-MSC and the hBM-MSCs, also evident were phenotypic differences between the populations especially between those that were cultured on human ECM (FIG. 6 E, 6F). The hAT-MSCs cultured on human ECM formed a lattice-like network throughout the culture dish, whereas the hBM-MSCs maintained canonical MSC morphology.

RT-PCR was performed as an additional means to quantify changes in RNA as a result of culture on different ECM substrates. A similar pattern of CCSP, cytokeratin-5 and SPC gene expression was observed in the hBM-MSC and hAT-MSC cultured on different ECM proteins by qPCR as seen by flow cytometry (FIG. 6C, 6D). However, qPCR data showed mixed human ECM protein resulted in significantly higher expression of SPC, lower expression of CCSP, and cytokeratin-5 genes in both hBM-MSC and hAT-MSC on day 7 compared to cells cultured on other ECM proteins.

Overall, both hAT-MSC and hBM-MSC populations undergo large changes in lung epithelial marker expression depending on the substrate on which they are cultured. Additionally, these data show that substrate alone can influence the expression of lung epithelial markers by mesenchymal stromal cells. These data provide insight into the differences in epithelial maker expression when comparing hAT-MSC and hBM-MSCs cultured in the lung bioreactor.

Finally, the phenotype of hBM-MSCs seeded onto decellularized liver matrix was analyzed when compared to the phenotype of hBM-MSCs following lung bioreactor culture (FIG. 11). hBM-MSCs were seeded onto decellularized liver slices and cultured for 3 days followed by immunostaining and H&E histological analysis. These data show that hBM-MSCs cultured in either 10% FBS/DMEM or in SAGM on liver slices do not express cytokeratin 5, CCSP, and only rarely express pro-SPC by immunostaining (FIG. 11). The culture period was restricted to only 3 days because longer periods resulted in lower MSC viability. These data further show that the remaining ECM following lung decellularization plays a role on the capability of MSCs to differentiate, and maintain expression of lung epithelial markers.

MSCs from Adipose and Bone Marrow are Capable of Taking a Type 2 Cell Phenotype and Function Following Culture in a Decellularized Rat Lung Bioreactor System Previous work has led to the development of a method to successfully decellularize rat lungs (Petersen et al., 2010, Science 329:538-541; Petersen et al., 2012, Cells Tissues Organs 195:222-231). These findings may ultimately allow for decellularized human lungs to be used as a scaffold onto which appropriate donor cells can be propagated and differentiated into lung epithelial cell types (Badylak et al., 2011, Annu Rev Biomed Eng 13:27-53). Characteristics that are essential for the donor cell type include: 1) the ability to differentiate into lung epithelial or other cell types; 2) be highly proliferative (must be able to expand these cells to high numbers prior to seeding onto the decellularized lung scaffolds); 3) be easily accessible from a patient (i.e. an autologous cell source, either differentiated or stem); and 4) lack of immunogenicity or triggering of immune response. In toto, these characteristics point to the possibility of using mesenchymal stromal cells as a source for reseeding decellularized lungs. hBM-MSCs have previously been shown to give rise to various epithelial cell types including lung epithelium, though some of these findings have remained controversial (Krause et al., 2001, Cell 105:1-9; Wong et al., 2009, Cytotherapy 11:676-687; Ortiz et al., 2003, PNAS 100:8408-8411; Wong et al., 2007, Am J Physiol Lung Cell Mol Physiol 293:L740-L752; Wang et al., 2006, Stem Cells 24:482-493). Additionally, MSCs are less immunogenic than most cell types, do not express MHC class 2 markers, and do not elicit a strong immune response as evidenced by lack of activation of T cells (Rasmusson et al., 2003, Transplantation, 76: 1208-1213). The present study of human marrow and adipose-derived MSCs in rat lung matrix point to clear and indisputable evidence of epithelial cell differentiation, at least to a type II alveolar cell phenotype, and perhaps other phenotypes as well.

The data presented herein demonstrate that human BM-MSCs, when placed onto decellularized rat lung matrices and cultured in SAGM, are capable of expressing the type 2 pneumocyte marker pro-SPC as well as the proximal airway marker cytokeratin-5. Previous work has failed to show any substantial contribution to lung epithelium from BM-MSCs that were seeded onto decellularized lung scaffolds (Daly et al, 2012, Tissue Eng Part A 18:1-16; Bonvillain et al., 2012, Tissue Eng Part A 18(23-24):2437-52). While not wishing to be bound by any particular theory, this discrepancy between the present data and the work of others may partly be explained by differences in the lung matrix decellularization process, and the use of continuous perfusion of media via the pulmonary artery in the bioreactor cultures utilized in the present study. In contrast, the work of these other groups used a lung slice culture system, and used a lung scaffold that likely differed in retained ECM components. Additionally, the decellularization method used here makes use of 8 mM CHAPS, whereas the other groups used 0.1% Triton-X in the decellularization protocol. A previous report comparing CHAPS and SDS detergents for decellularization found differences in retention of collagen and elastin following lung decellularization (Petersen et al., 2012, Cells Tissues Organs 195:222-231). It is likely that different matrix components remain following CHAPS lung decellularization as compared with Triton-X decellularization, and as a result there is an influence on the differentiation of the seeded BM-MSCs. Another, albeit more remote possibility for the discrepancy between reports, is that the present study used human derived MSCs seeded onto rat lungs, whereas Daly and colleagues used mouse lungs and cells, and Bonvillain et al. used both macaque lungs and cells.

It is also shown herein that hAT-MSCs give rise to Clara-like cells that line the airways and express CCSP protein, a characteristic that is not found in any of the three human bone marrow donor samples assayed. Additionally, similar to hBM-MSCs, hAT-MSCs also give rise to type 2-like cells, but do not give rise to cells that are positive for cytokeratin-5 after recellularizing the lung. These differences are particularly interesting given that both MSC sources start out with common CD marker expression. However, as shown herein, the MSC populations vary with regard to the populations that express the epithelial markers CCSP, pro-SPC and cytokeratin-5. These differences in initial epithelial marker expression may result in the downstream variation between the MSC sources after culture in the lung bioreactor. Various reports have documented a difference with regard to differentiation potential of MSCs depending on the tissue of origin (Vidal et al., 2008, Veterinary Surgery 37:713-724; Baer & Geiger, 2012, Stem Cells International 2012, 1-11; Al-Nbaheen et al., 2013, Stem Cell Rev 9(1):32-43; Hoffman et al., 2011, Stem Cells and Development 20:1779-1792; Pevsner-Fischer et al., 2011, Stem Cell Rev and Rep 7:560-568). Gene expression comparisons between MSCs derived from bone marrow, adipose and skin has shown a marked difference in the ability to express genes associated with osteogenic and adipogenic lineages (Al-Nbaheen et al., 2013, Stem Cell Rev 9(1):32-43). Given the present results when comparing hAT-MSC and hBM-MSC sources, while not wishing to be bound by any particular theory, it is likely that additional MSC sources may have distinct differentiation potential when cultured under appropriate lung biomimetic conditions. A particularly interesting candidate to assess are cells isolated from bronchoalveolar lavage fluid, so called "lung MSCs" that attach to plastic and express canonical markers associated with bone marrow MSCs (Hoffman et al., 2011, Stem Cells and Development 20:1779-1792; Lama et al., 2007, J Clin Invest 117:989-996; Jarvinen et al., 2008, J Immunol. 181(6):4389-96).

While previous studies have shown the ability of BM-MSCs to differentiate into lung epithelium, these findings are not without controversy (Kassmer & Krause, 2010, Experimental Hematology 38:564-573). These controversies largely appear to derive from variations in experimental methods used between investigators, particularly the use of eGFP as a means to lineage trace cells of interest (Krause, 2008, Proc Am Thorac Soc 5:323-327). The present results further solidify the capability of hBM-MSCs to contribute to lung epithelium, since the starting material is decellularized lung and hBM-MSCs or hAT-MSC. The decellularized lung in the present study is completely devoid of lung epithelial cells (FIG. 2B). This leaves out the possibility of contaminating, non-bone marrow or adipose derived cells being misinterpreted as lung epithelium.

It was also set out to show that the recellularized lung had a functional improvement when compared to the acellular lung scaffold. One of the main functions of alveolar type 2 cells is the production of surfactant protein. While both hAT-MSC and hBM-MSC populations expressed surfactant protein C by immunofluorescence, RT-PCR and contained lamellar bodies as shown by TEM, it is also shown that the MSCs cultured in recellularized lung actively produce SPC by ELISA, and also contain visible surfactant droplets in the medium adjacent to the lung slices. The data presented herein indicate that the hAT-MSCs are able to secrete up to 5.5 ng/mL of SPC into the media when compared to 3.3 ng/mL SPC secreted by hBM-MSC at day 3 in culture. These data further support that MSCs are capable of taking a type-2 cell phenotype, but also are capable of producing surfactant while attached to the decellularized lung matrix. Interestingly, there was no visual evidence of surfactant secretion in cultures maintained in 10% FBS from either MSC population, in support of the importance of the culture medium in cellular differentiation (FIG. 5 and FIG. 8).

In order to assess the importance of the ECM in modulating cell differentiation MSCs were also cultured in SAGM in different kinds of ECM and assessed gene expression levels for several epithelial markers by RT-PCR and population marker expression was assessed by FACS analysis. These data show that the MSC populations markedly vary in terms of marker expression when grown on different ECM substrate. In a related experiment, hBM-MSCs were cultured on decellularized liver in either SAGM or 10% FBS for 3 days (FIG. 11). These experiments were aimed at answering a particularly fundamental, yet surprisingly not often assessed question of the importance and influence of the retained ECM on the differentiation of cells following culture on decellularized organs. These experiments showed that hBM-MSCs do not express cytokeratin-5 and largely are negative for pro-SPC expression following culture on the acellular liver.

Collectively, these experiments demonstrate that MSCs from both adipose and bone marrow are capable of taking a type 2 cell phenotype and function following culture in a decellularized rat lung bioreactor system, while only hAT-MSCs are capable of colonizing the airways with CCSP positive cells. These data are of importance because future lung recellularization efforts may make use of various MSC sources as donor cells for whole organ repopulation. To this end the potential of alternate MSC sources including those derived from the umbilical cord and lung tissue are being explored, either in isolation or in co-culture scenarios to enhance the recellularization process.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A population of epithelial lung cells seeded on a substrate, wherein the cells are differentiated from adipose tissue-derived mesenchymal stem cells (AT-MSCs), wherein the epithelial lung cells comprise at least 95% Clara cells that express at least one epithelial marker comprising CCSP and do not express cytokeratin-5.

2. The population of lung cells seeded on the substrate of claim 1, wherein the substrate is a decellularized lung tissue.

3. The population of lung cells seeded on the substrate of claim 1, wherein the substrate is a coating comprising an extracellular matrix.

4. The population of lung cells seeded on the substrate of claim 3, wherein the extracellular matrix comprises one or more of human ECM, laminin, fibronectin, collagen IV, and collagen I.

5. The population of lung cells seeded on the substrate of claim 1, wherein the population comprises genetically modified cells.

6. The population of lung cells seeded on the substrate of claim 5, wherein the genetically modified cells are the epithelial lung cells genetically modified to express a therapeutic gene.

7. The population of lung cells seeded on the substrate of claim 1, wherein the cells are differentiated from the AT-MSCs according to a method comprising:
   seeding the AT-MSCs on the substrate ex vivo; and
   exposing the AT-MSCs seeded substrate to small airway growth medium that comprises at least one of retinoic acid and human epidermal growth factor, thereby differentiating the AT-MSCs.

* * * * *

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
ccttcttatc gtggtggtgg t                                       21

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2
tctccgtgtg tttctggctc at                                      22

<210> SEQ ID NO 3
<211> LENGTH: 20
<212> TYPE: DNA
<213> ORGANISM: Artificial Sequence
<220> FEATURE:

```
<223> OTHER INFORMATION: Synthetic

<400> SEQUENCE: 3
actgggtttt ctgggtaggg                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
atggtcttct tccgctcttc                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
ctacaagccc aacaacaagg                                              20

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
catcgttgag gtgtttaggg t                                            21

<210> SEQ ID NO 7
<211> LENGTH: 23
<212> TYPE: DNA
<213> ORGANISM: Artificial Sequence
<220> FEATURE:
<223> OTHER INFORMATION: Synthetic

<400> SEQUENCE: 7
gacaacagcc tcaagatcat cag                                          23

<210> SEQ ID NO 8
<211> LENGTH: 23
<212> TYPE: DNA
<213> ORGANISM: Artificial Sequence
<220> FEATURE:
<223> OTHER INFORMATION: Synthetic

<400> SEQUENCE: 8
atggcatgga ctgtggtcat gag                                          23
```